United States Patent
Shah et al.

(10) Patent No.: US 10,350,329 B2
(45) Date of Patent: Jul. 16, 2019

(54) GRAPHENE-BASED INK COMPOSITIONS FOR THREE-DIMENSIONAL PRINTING APPLICATIONS

(71) Applicant: Northwestern University, Evanston, IL (US)

(72) Inventors: Ramille N. Shah, Hinsdale, IL (US); Adam E. Jakus, Chicago, IL (US); Mark C. Hersam, Wilmette, IL (US); Ethan B. Secor, Evanston, IL (US)

(73) Assignee: NORTHWESTERN UNIVERSITY, Evanston, IL (US)

(*) Notice: Subject to any disclaimer, the term of this patent is extended or adjusted under 35 U.S.C. 154(b) by 0 days.

(21) Appl. No.: 15/500,339

(22) PCT Filed: Oct. 15, 2015

(86) PCT No.: PCT/US2015/055773
§ 371 (c)(1),
(2) Date: Jan. 30, 2017

(87) PCT Pub. No.: WO2016/085584
PCT Pub. Date: Jun. 2, 2016

(65) Prior Publication Data
US 2017/0209622 A1    Jul. 27, 2017

Related U.S. Application Data

(60) Provisional application No. 62/064,338, filed on Oct. 15, 2014.

(51) Int. Cl.
*A61L 27/44* (2006.01)
*A61L 27/08* (2006.01)
(Continued)

(52) U.S. Cl.
CPC ............ *A61L 27/443* (2013.01); *A61L 27/08* (2013.01); *A61L 27/38* (2013.01); *A61L 27/56* (2013.01);
(Continued)

(58) Field of Classification Search
CPC .. A61L 27/08; A61L 2400/12; A61L 2400/18; A61L 27/443; A61L 27/507;
(Continued)

(56) References Cited

U.S. PATENT DOCUMENTS

| | | |
|---|---|---|
| 5,518,680 A | 5/1996 | Cima et al. |
| 6,582,651 B1 | 6/2003 | Cochran, Jr. et al. |

(Continued)

FOREIGN PATENT DOCUMENTS

| | | |
|---|---|---|
| EP | 0393747 | 10/1990 |
| JP | 1997(H9)-502999 A | 3/1997 |

(Continued)

OTHER PUBLICATIONS

Kyriakidou et al., Dynamic Co-Seeding of Osteoblast and Endothelial Cells on 3D Polyoaprolactone Scaffolds for Enhanced Bone Tissue Engineering, Journal of Bioactive and Compatible Polymers, vol. 23, May 2008, pp. 227-243.

(Continued)

*Primary Examiner* — Camie S Thompson
(74) *Attorney, Agent, or Firm* — Bell & Manning, LLC

(57) ABSTRACT

Electrically conducting, biocompatible, biodegradable tissue growth comprising graphene flakes in a polymeric matrix are provided.

23 Claims, 28 Drawing Sheets

(51) Int. Cl.
*A61L 27/38* (2006.01)
*A61L 27/56* (2006.01)
*C09D 11/102* (2014.01)
*C09D 11/52* (2014.01)
*C09D 11/033* (2014.01)
*C09D 11/037* (2014.01)
*C09D 11/10* (2014.01)
*C09D 11/104* (2014.01)
*B29C 64/165* (2017.01)

(52) U.S. Cl.
CPC .......... *B29C 64/165* (2017.08); *C09D 11/033* (2013.01); *C09D 11/037* (2013.01); *C09D 11/10* (2013.01); *C09D 11/102* (2013.01); *C09D 11/104* (2013.01); *C09D 11/52* (2013.01)

(58) Field of Classification Search
CPC .............. A61L 27/3895; A61L 27/3804; A61L 2430/20; A61L 2430/30; A61L 2430/34; B82Y 30/00; B82Y 40/00; C08L 2201/011; C08L 67/04; C08K 3/04; C08K 3/042; A61K 8/0254; C12M 24/14; C12N 2533/40; C09D 7/70; Y10T 428/2982; A61F 2/08; A61F 2/28; A61F 2/442; A61F 2/02
See application file for complete search history.

(56) References Cited

U.S. PATENT DOCUMENTS

| | | | |
|---|---|---|---|
| 9,327,448 | B2 | 5/2016 | Shah et al. |
| 2001/0008317 | A1 | 7/2001 | Gaylo et al. |
| 2002/0103538 | A1 | 8/2002 | Hughes et al. |
| 2003/0236513 | A1 | 12/2003 | Schwarz |
| 2004/0186139 | A1 | 9/2004 | Reddy et al. |
| 2005/0003189 | A1 | 1/2005 | Bredt et al. |
| 2005/0202058 | A1 | 9/2005 | Hiles |
| 2006/0292350 | A1 | 12/2006 | Kawamura et al. |
| 2008/0004359 | A1 | 1/2008 | Ma et al. |
| 2008/0145639 | A1 | 6/2008 | Sun et al. |
| 2009/0117087 | A1 | 5/2009 | Carroll et al. |
| 2009/0208466 | A1 | 8/2009 | Yoo et al. |
| 2010/0000441 | A1 | 1/2010 | Jang et al. |
| 2010/0096596 | A1 | 4/2010 | Lewis et al. |
| 2010/0136114 | A1 | 6/2010 | Mao |
| 2010/0279007 | A1 | 11/2010 | Briselden et al. |
| 2011/0064784 | A1 | 3/2011 | Mullens et al. |
| 2011/0196094 | A1 | 8/2011 | Hamad et al. |
| 2011/0223405 | A1* | 9/2011 | Compton ............... B82Y 30/00 428/220 |
| 2013/0195955 | A1 | 8/2013 | Reichert et al. |
| 2014/0271961 | A1 | 9/2014 | Khoshnevis |
| 2015/0012092 | A1* | 1/2015 | Schroeder ............. A61L 27/443 623/13.11 |
| 2015/0037385 | A1 | 2/2015 | Shah et al. |
| 2015/0076732 | A1 | 3/2015 | Kemmer et al. |
| 2015/0125952 | A1* | 5/2015 | Kim ........................ A61L 27/14 435/366 |
| 2015/0315449 | A1* | 11/2015 | Kim ........................ C09K 5/14 165/185 |
| 2016/0032062 | A1* | 2/2016 | Clauss ................... C08K 3/042 523/468 |
| 2017/0081534 | A1 | 3/2017 | Shah et al. |

FOREIGN PATENT DOCUMENTS

| | | |
|---|---|---|
| JP | 2006-504813 A | 2/2006 |
| JP | 2010-536694 A | 12/2010 |
| JP | 2010-537679 A | 12/2010 |
| WO | WO 95/11007 A1 | 4/1995 |
| WO | WO0069008 | 11/2000 |
| WO | WO 2004/028787 A1 | 4/2004 |
| WO | WO 2009/023226 A2 | 2/2009 |
| WO | WO 2004/027525 A2 | 3/2009 |
| WO | WO2013180662 | 12/2013 |
| WO | WO2014210584 | 12/2014 |
| WO | WO2015102746 | 7/2015 |

OTHER PUBLICATIONS

Jakus et al., 3D-Bioplotted Elastic Bone Scaffolds for Tissue Engineering Applications, Poster Presentation, Oral Biology Centennial, University of Chicago, Jun. 19, 2013.

Jakus et al., Bioplotted Elastic Hydroxyapatite-Based Tissue Engineering Scaffolds, Oral Presentation, TMS Pacific Rim International Congress on Advanced Materials and Processing, Waikoloa, HA , Aug. 6, 2013.

Jakus et al., A Single Platform 3D-Printing Approach for Fabricating Tissue Engineering Bio-Scaffolds from Multiple Material Systems, Oral Presentation, Materials Science and Engineering 2013 Hilliard Symposium, Northwestern University, Evanston, May 16, 2013.

Michna et al., Concentrated hydroxyapatite inks for direct-write assembly of 3-D periodic scaffolds, Biomaterials, vol. 26, Apr. 21, 2005, pp. 5632-5639.

Shuai et al., Fabrication of porous polyvinyl alcohol scaffold for bone tissue engineering via selective laser sintering, Biofabrication, vol. 5, No. 015014, Feb. 6, 2013, pp. 1-8.

R. Shah, The Use of 3D Bioplotted Scaffolds and Ultrasonic Stimulation for Tissue Engineering, Oral Presentation, Oral Biology Centennial, University of Chicago, Jun. 19, 2013, slides 1-24.

Yeo et al., Preparation and Characterization of 3D Composite Scaffolds Based on Rapid-Prototyped PCL/β-TCP Struts and Electrospun PCL Coated with Collagen and HA for Bone Regeneration, Chem. Mater., vol. 24, Jul. 5, 2011, pp. 903-913.

Jakus et al., Biochemically Active Bioplotted Elastic Hydroxyapatite-Based Tissue Engineering Scaffolds: Structural, Mechanical, and in vitro Evaluation, Abstract for Presentation at TMS Pacific Rim International Congress on Advanced Materials and Processing Waikoloa, HA, Aug. 7, 2013.

Jakus et al., 3D-Printed Hyperelastic Bone for Hard-Tissue Engineering Applications, Abstract for Presentation at Hilliard Symposium, Northwestern University, May 15, 2014.

Intl. Search Report & Written Opinion issued for Intl. Patent Appl. No. PCT/US2015/030972, dated Aug. 26, 2015, 15 pp.

Calvert et al., Solid freeform fabrication of organic-inorganic hybrid materials., Materials Science and Engineering: C 6.2, 1998, pp. 167-174.

Hong et al., Microstructure and Mechanical Properties of Reticulated Titanium Scrolls, Advanced Engineering Materials, vol. 13, No. 12, 2011, pp. 1122-1127.

Jakus et al., Bioplotted Ceramics and Metals: A Universal Technique for Fabricating Complex, Ordered, and Functional Scaffolds, The 8th Pacific Rim International Congress on Advanced Materials and Processing, Abstract, Aug. 1, 2013.

A. Thorel, Tape Casting Ceramics for high temperature Fuel Cell applications, Ceramic Materials, Wilfried Wunderlich (Ed.), ISBN: 978-953-307-145-9, InTech, Sep. 28, 2010, pp. 49-68.

Falcade et al., Fuel Cell: A Review and a New Approach About YSZ Solid Oxide Electrolyte Deposition Direct on LSM Porous Substrate by Spray Pyrolysis, New Advances in Fundamental Researches and Applications, Dr. Yan Shao (Ed.), ISBN: 978-953-51-0032-4, InTech, Mar. 7, 2012, pp. 139-160.

International Search Report and Written Opinion mailed in PCT/US2015/055773, dated Jul. 25, 2016.

Das et al., Graphene-based polymer composites and their applications, Polymer-Plastics Technology and Engineering, Feb. 27, 2013, vol. 52, No. 4, pp. 319-331.

Leigh et al., A simple, low-cost conductive composite material for 3D printing of electronic sensors, PLoS One, Nov. 21, 2012, vol. 7, No. 11, e49365, internal pp. 1-6.

(56) References Cited

OTHER PUBLICATIONS

Guo et al., Properties of polylactide inks for solvent-cast printing of three-dimensional freeform microstructures, Langmuir, Jan. 11, 2014, vol. 30, No. 4, pp. 1142-1150.

Jakus et al., Three-dimensional printing of high-content grapheme scaffolds for electronic and biomedical applications, ACS NANO, Apr. 10, 2015, vol. 9, No. 4, pp. 4636-4648.

International Search Report and Written Opinion mailed in PCT/US2016/026342, dated Jul. 12, 2016.

Cesaretti et al., Building components for an outpost on the Lunar soil by means of a novel 3D printing technology, Acta Astronautica, vol. 93, Aug. 8, 2013, pp. 430-450.

Zhao et al., 3D-Printing on Mars: Trade-off Between In-situ Spare Parts Production on Mars and Spare Parts Supply From Earth, Jul. 2014.

Jaycox et al., 3-D Printing Lunar and Martian Dusts From Liquid 3D-Inks, Poster Presentation at ASM Chicago on Apr. 8, 2014.

Méndez-Ramos et al., Prospective use of the 3D printing technology for the microstructural engineering of Solid Oxide Fuel Cell components, Boletín de la Sociedad Española de Cerámica y Vidrio, vol. 53, Sep. 2014, pp. 213-216.

Jakus et al., 3D Printed Solid Oxide Fuel Cells from High Particle Content Liquid Inks, MRS Fall 2014 Meeting, Dec. 3, 2014.

Ahn et al., Printed Origami Structures, Advanced Materials 22, May 25, 2010.

Farandos et al., 3D Printing of Functional Layers for Solid Oxide Fuel Cells and Electrolysers, ECS Conference on Electrochemical Energy Conversion & Storage with SOFC-XIV, Jul. 26, 2015, Glasgow, Scotland.

Sun et al., 3D Printing of Interdigitated Li-Ion Microbattery Architectures, Advanced Materials 25, Jun. 17, 2013, pp. 4539-4543.

S. Taylor, Lomiko Metals Announce 3D Printing Graphene Patent, Jan. 21, 2014.

Subramanian et al., Development of biomaterial scaffold for nerve tissue engineering: Biomaterial mediated neural regeneration, Journal of Biomedical Science, Nov. 25, 2009.

Ahn et al., Carbon-nanotube-interfaced glass fiber scaffold for regeneration of transected sciatic nerve, Acta Biomaterialia 13, Nov. 21, 2014, pp. 324-334.

Extended European search report mailed in European Application No. 15792640.3, dated Oct. 19, 2017.

\* cited by examiner

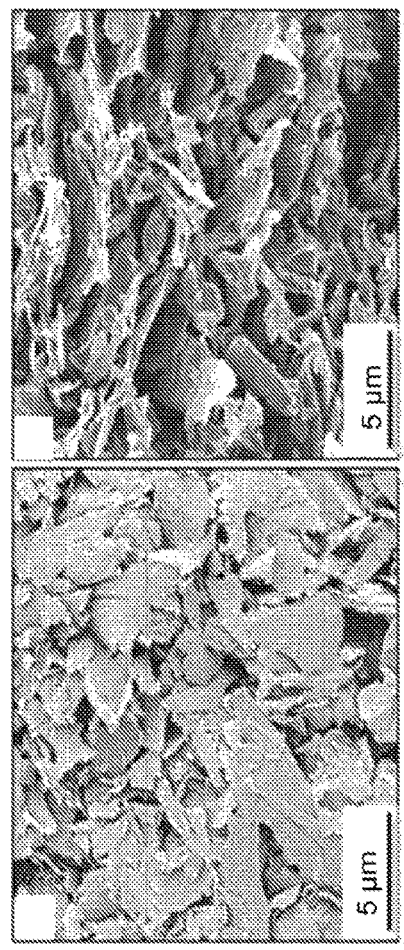
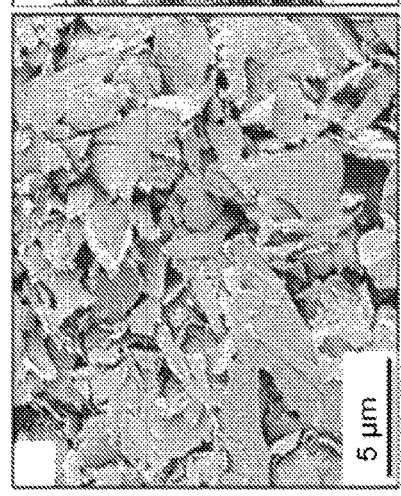
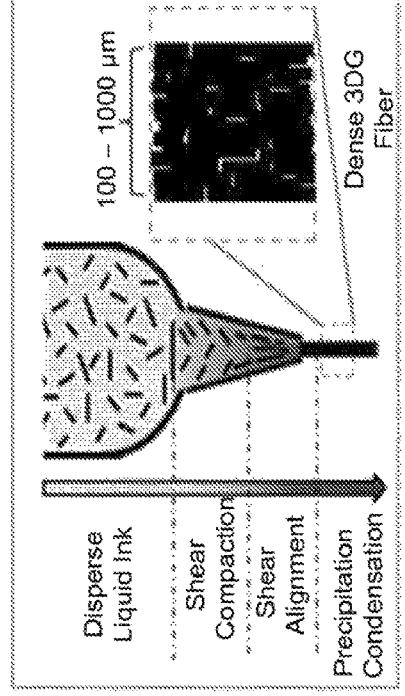
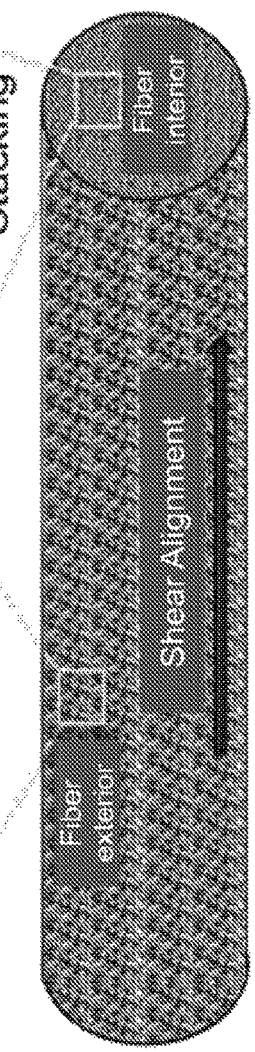
FIG. 2A  FIG. 2B  FIG. 2C  FIG. 2D

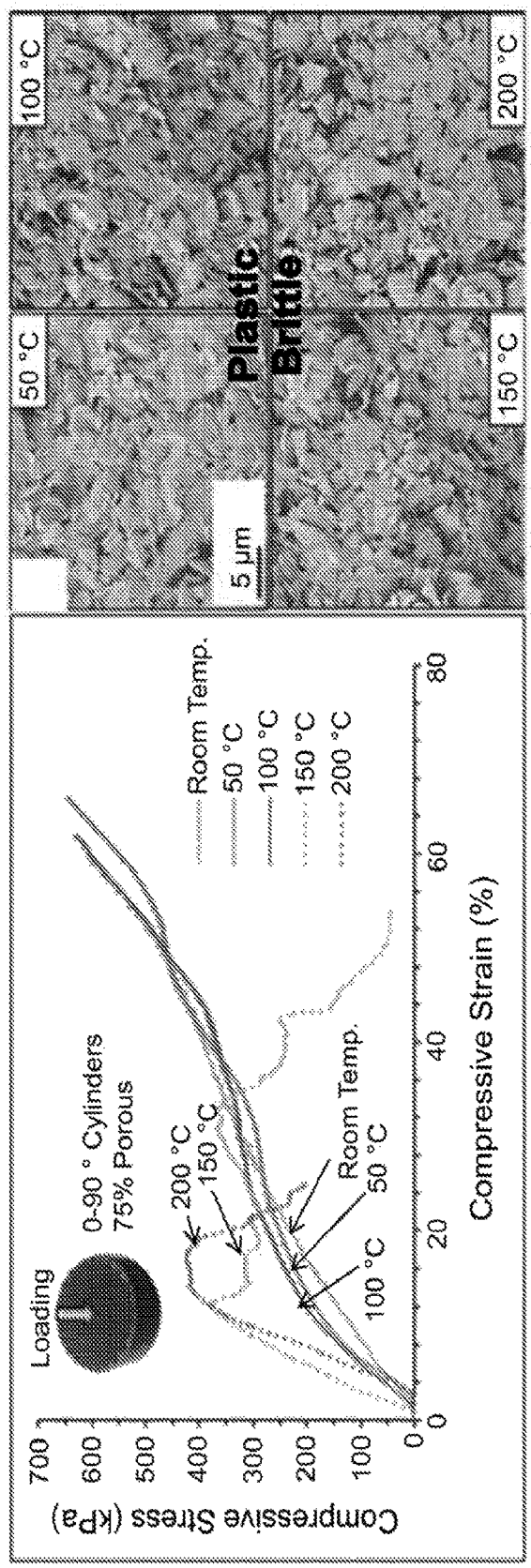
FIG. 3D
FIG. 3E
FIG. 3F

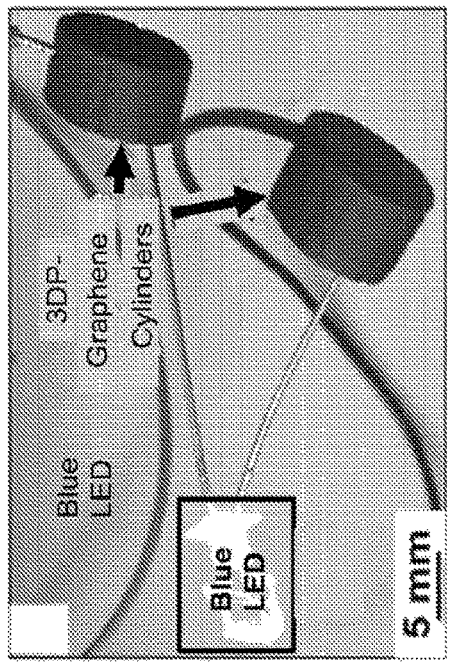
FIG. 4A
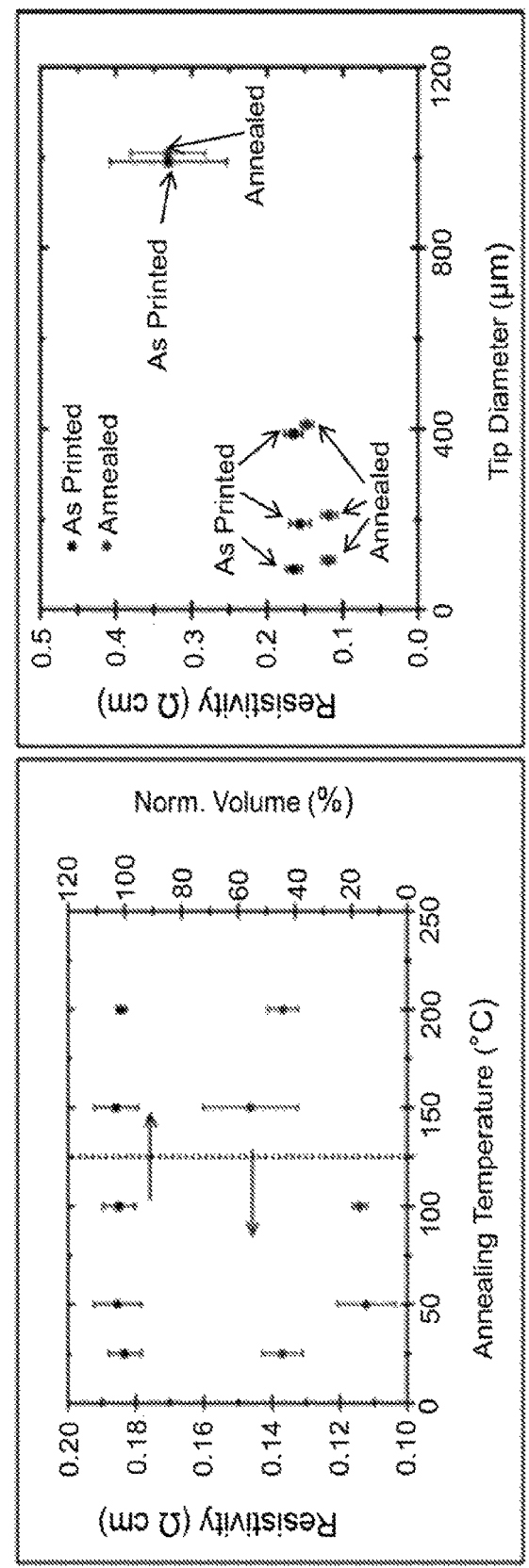
FIG. 4B
FIG. 4C

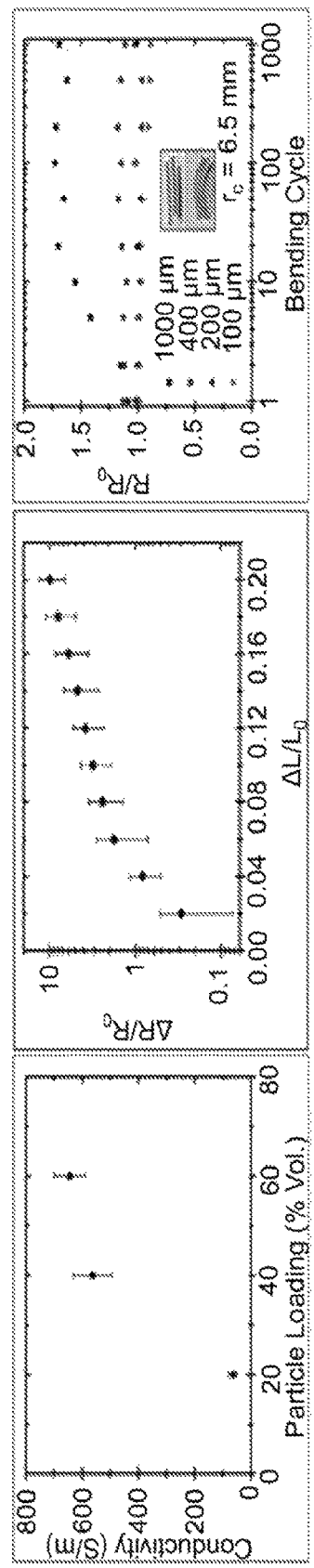

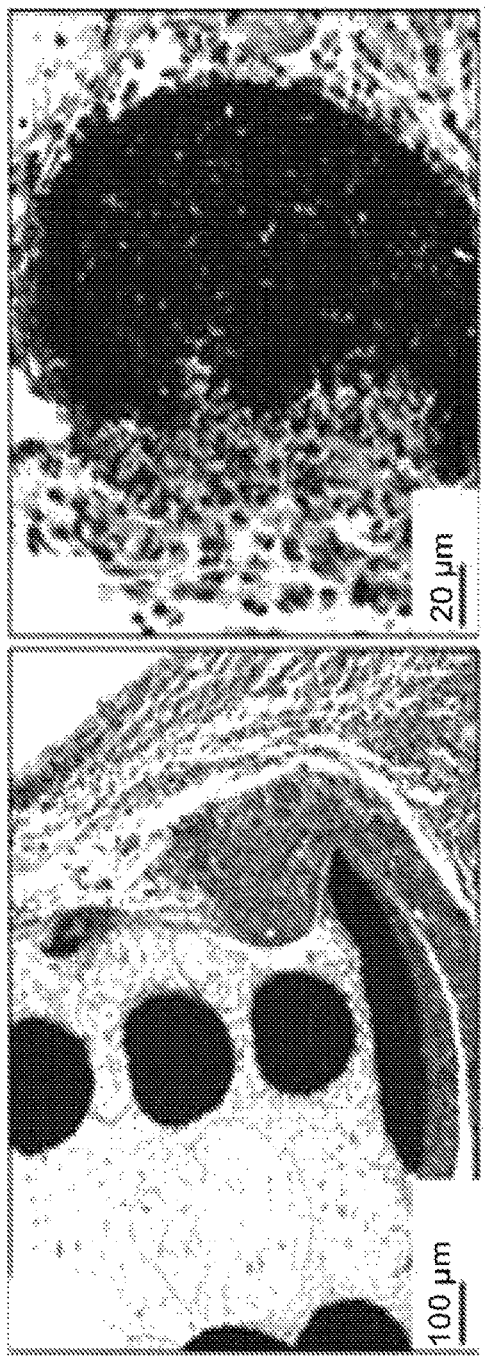
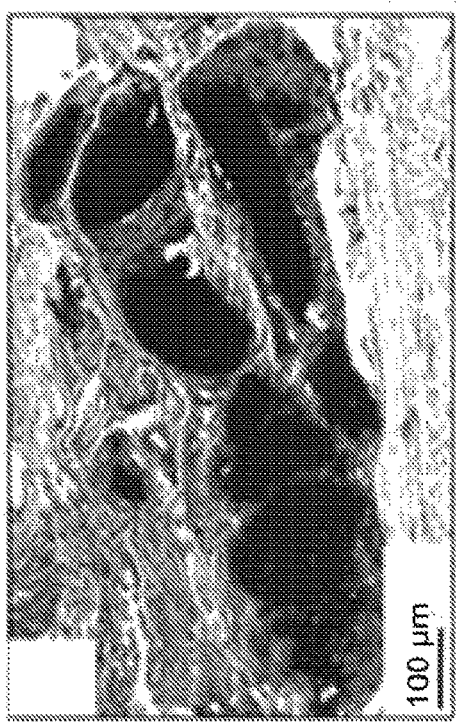

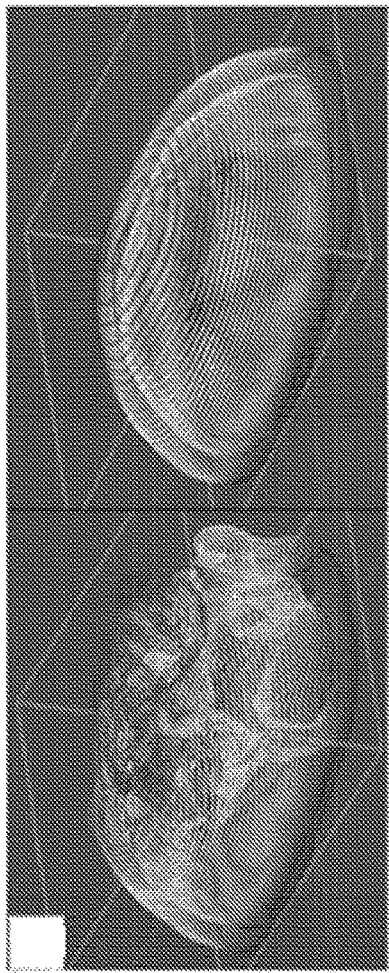
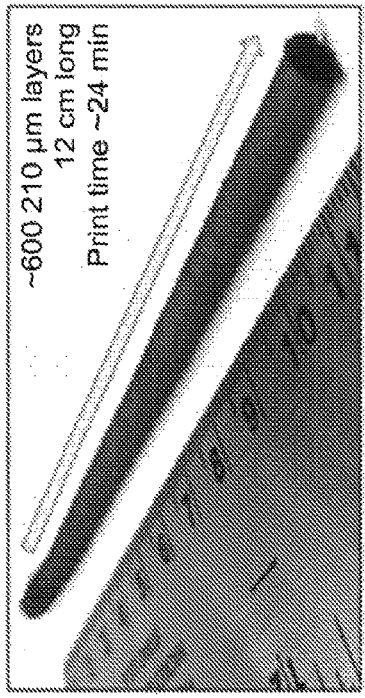
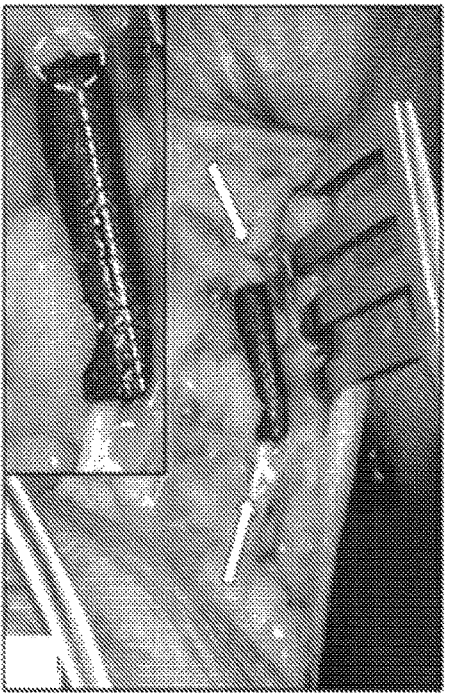
FIG. 7H
FIG. 7I
FIG. 7F
FIG. 7G

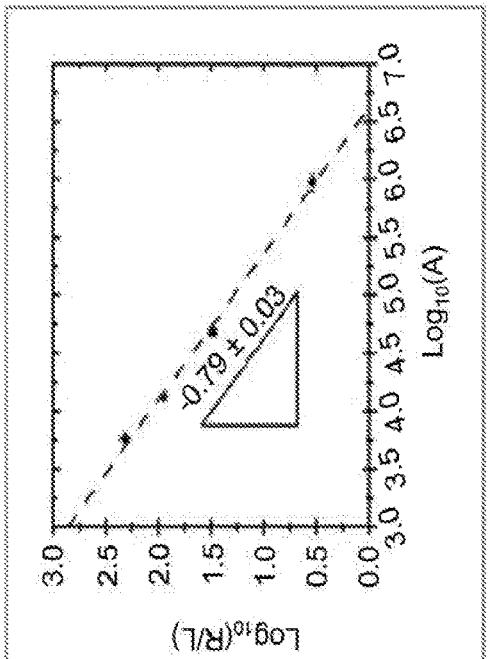
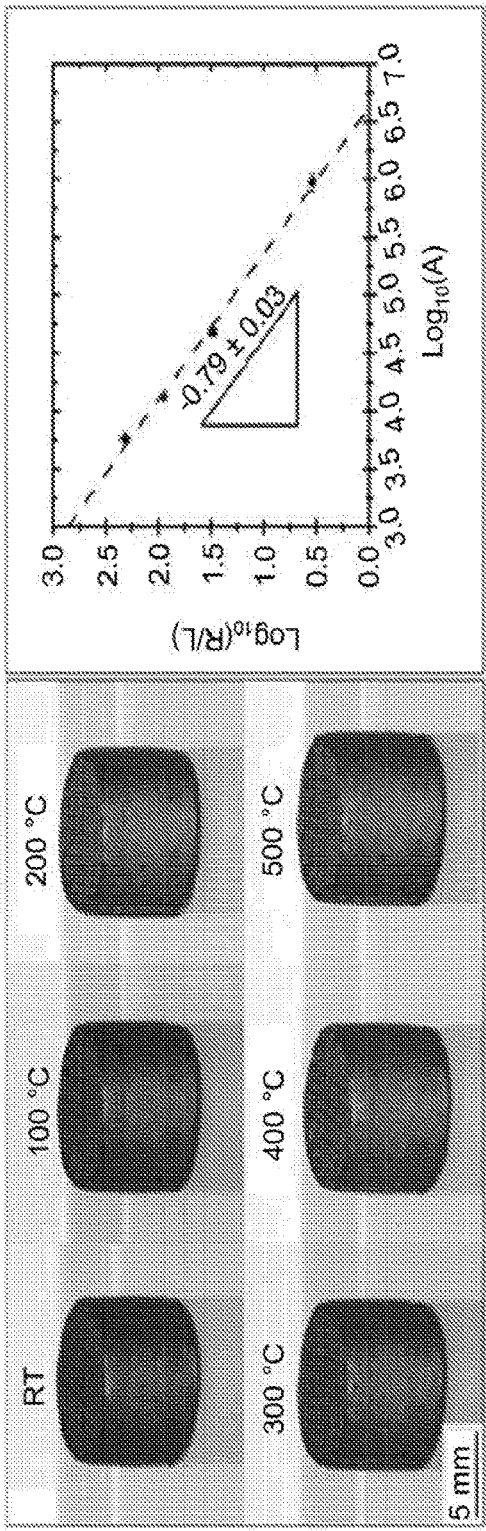
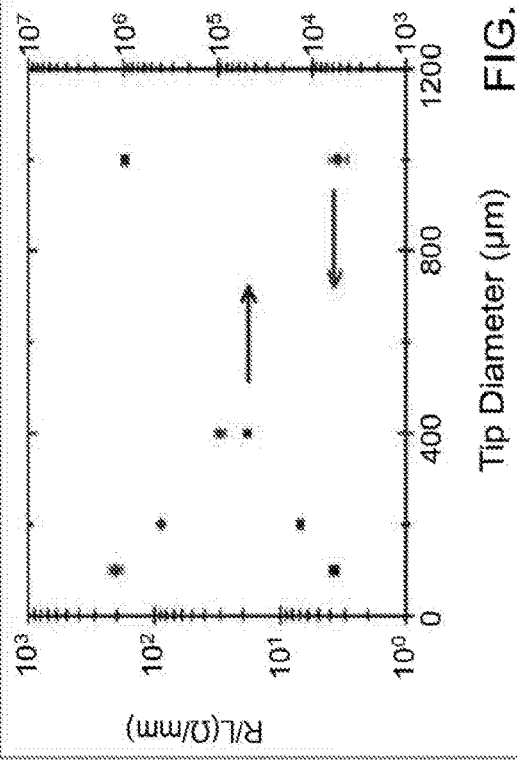

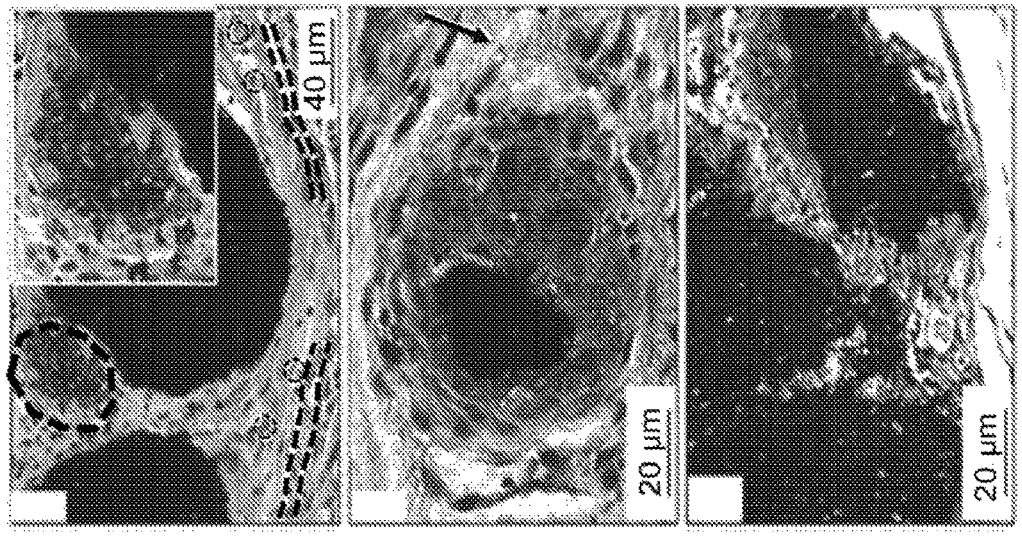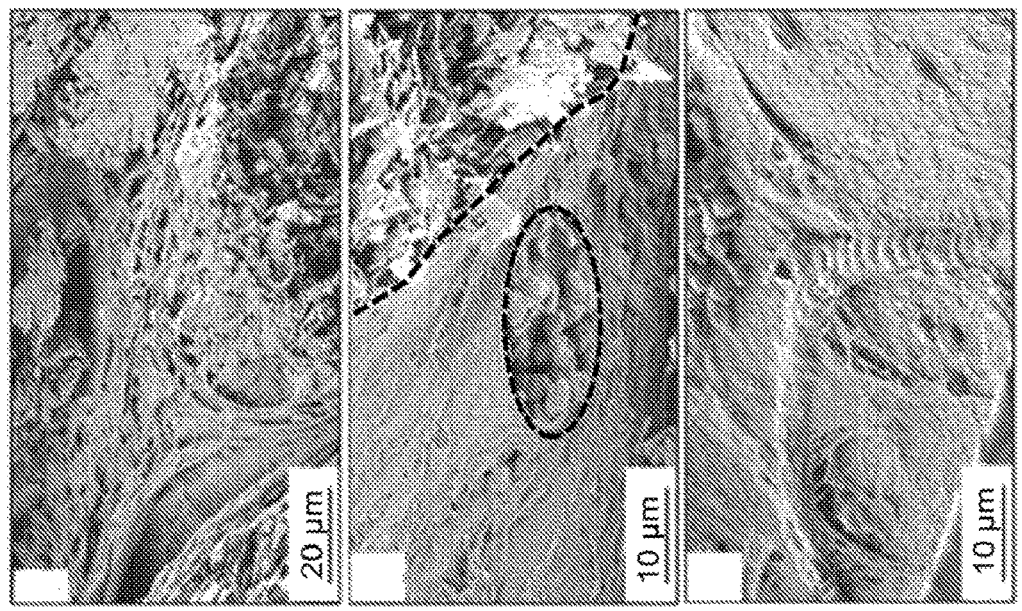

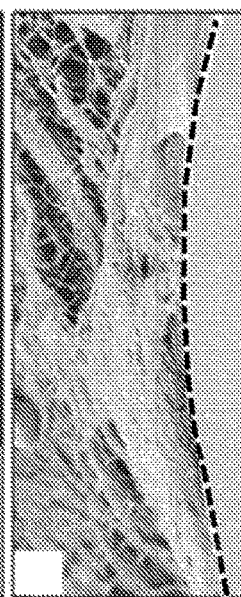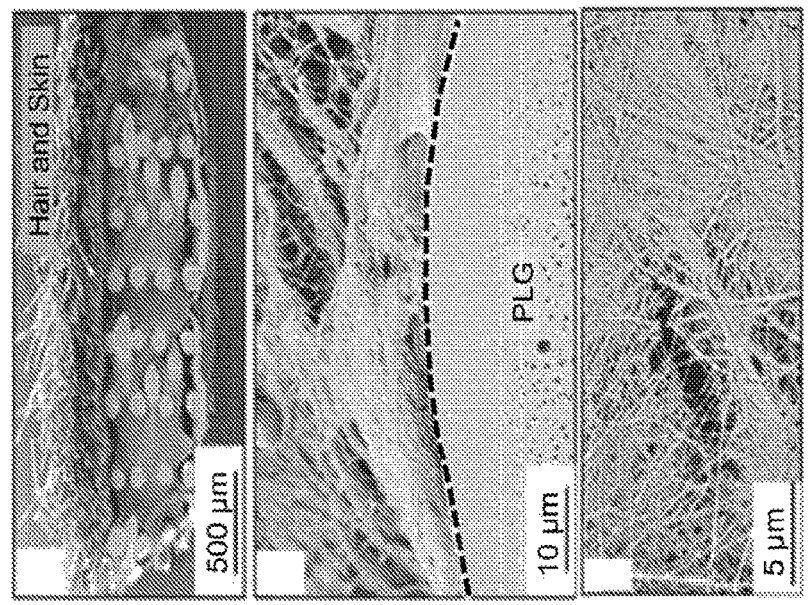
FIG. 11D  FIG. 11E  FIG. 11F
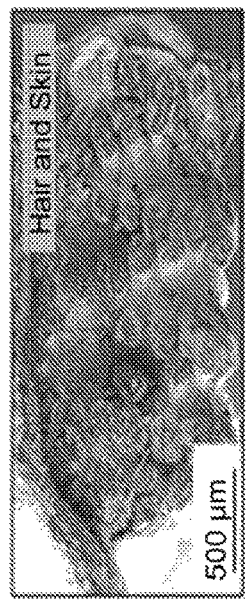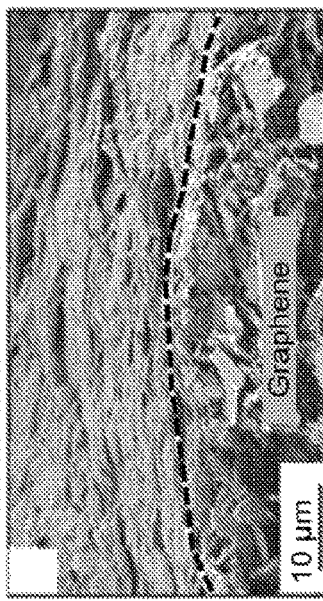
FIG. 11A  FIG. 11B  FIG. 11C

GRAPHENE-BASED INK COMPOSITIONS FOR THREE-DIMENSIONAL PRINTING APPLICATIONS

CROSS-REFERENCE TO RELATED APPLICATIONS

The present application is a National Stage Entry of International Application No. PCT/US2015/055773 that was filed on Oct. 15, 2015, the entire contents of which are hereby incorporated by reference; which claims priority to U.S. Provisional Patent Application No. 62/064,338 that was filed Oct. 15, 2014, the entire contents of which are hereby incorporated by reference.

REFERENCE TO GOVERNMENT RIGHTS

This invention was made with government support under grant number N00014-11-1-0690 awarded by the Office of Naval Research and grant number DMR-1121262 awarded by the National Science Foundation. The government has certain rights in the invention.

BACKGROUND

Graphene has been the focus of significant interest in both academic and industrial settings. With exceptional electronic, mechanical, and thermal properties, it is widely hailed for a range of applications from high-speed electronics and energy storage devices to electrochemical sensors. More recently, it has been used as a new biocompatible, conductive biomaterial for drug delivery, stem cell differentiation, biosensors, imaging, and osteo, cardiac, and neuro tissue engineering and regeneration. The direct manipulation of graphene, on micro- and macroscopic scales, is desirable for many of these applications. In this regard, digital, additive, and solution-phase printing technologies offer a promising approach. For example, inkjet and gravure printing of graphene have been demonstrated for a range of devices including transistors, supercapacitors, transparent conductors, and interconnects. While significant and having many applications, demonstrations to date remain limited to thin film, paper, or hydrogel composite formats.

Three-dimensional (3D) printing is widely considered a revolutionary manufacturing technology, with significant promise in a broad range of fields including tissue and organ engineering. Direct ink writing is an extrusion-based 3D printing technique involving the deposition of a liquid material ink that rapidly solidifies upon extrusion and allows the fabrication of 3D objects layer-by-layer. Direct ink writing is also compatible with multi-material printing, offering a distinct advantage for integrating multiple functionalities in a 3D printing format. Further development of materials compatible with 3D printing will continue to expand its scope and impact. While carbon-composite inks have been previously developed for 3D printing applications, graphene-based inks offer enhanced functionality and improved electrical, mechanical, and biological properties.

SUMMARY

Ink compositions comprising graphene flakes and methods of printing the ink compositions into structures comprising graphene composites are provided. Also provided are implantable tissue growth structures made from the inks, including neural tissue growth scaffolds, methods of forming the tissue growth structures using 3D printing techniques, and methods for growing tissue on the tissue growth scaffolds.

One embodiment on an ink composition comprises a solids content, said composition comprising: a fluid composition comprising a plurality of components providing said fluid composition a volatility gradient; a polymer component providing less than 50 vol. % of said composition solids content; and graphene comprising greater than 50 vol. % of said composition solids content.

One embodiment of a graphene composite comprises: graphene particles; and a polymer matrix component about said graphene particles, said composite having a solids content, and said graphene particles providing greater than 50 vol. % of said composite solids content.

One embodiment of a method of preparing a three-dimensional graphene article comprises the steps of: providing a graphene ink composition comprising a solids content, said ink composition comprising a fluid composition comprising at least one solvent component, a biodegradable polymer component and a graphene component; applying said graphene ink composition to selected positions on a substrate, said selected positions corresponding to an article of manufacture, said application providing a plurality of layers of said graphene ink composition; and forming a solid layer-by-layer construction of said article of manufacture.

One embodiment of an implantable tissue growth structure comprises a three-dimensional, biocompatible, biodegradable, electrically conductive structure, wherein the structure comprises a composite of graphene flakes in a polymeric matrix and further wherein the composite has a graphene flake content of at least 20 vol. %. In some embodiments, the composite has a graphene flake content of at least 40 vol. %.

One embodiment of a method for generating electrogenic cells or tissues comprises: contacting a three-dimensional, biocompatible, biodegradable, electrically conductive scaffold with electrogenic cells or electrogenic tissue, wherein the scaffold comprises a composite comprising graphene flakes n a polymeric matrix and further wherein the composite has a graphene flake content of at least 40 vol. %, wherein electrogenic cell generation takes place on the scaffold. The scaffold can be seeded with biological cells, such as stem cells, and can be cultured in a culture medium or implanted in a living subject for tissue engineering applications.

BRIEF DESCRIPTION OF THE DRAWINGS

It should be understood that the drawings and descriptions are provided solely for the purpose of illustrating certain representative, non-limiting embodiments of this invention, together with certain non-limiting principles and aspects thereof. The drawings are not intended to limit the scope of the present invention in any way.

FIGS. 2A-G. (A) 3DG (60% by volume graphene, 40% PLG) inks are liquid prior to extrusion. Upon application of pressure and flow into the narrowing diameter nozzle, shear forces result in graphene flake alignment. Upon exiting the nozzle, DCM rapidly evaporates, solidifying the fiber and resulting in a slight diameter reduction. (B,C) Scanning electron microscopy (SEM) images of the fiber exterior and cross section, respectively, reveal that this process results in flake alignment along the exterior of the fibers and flake stacking within the fibers. (D) Example illustrating the measurement of flake orientation in an end-on cross sectional view of the 3DG fiber. (E) Histogram of graphene flake orientations with respect to the horizontal. The distribution around 0° indicates that there is a preferential alignment of the flakes within the fiber interior. (F) SEM and optical (inset) images of 3DG structures printed with a 100 µm tip, displaying a high degree of regularity. (G) Uniformity of 3DG structure quantified by fiber thickness in a 40-layer construct printed with a 100 µm tip. While the first layer deviates from the mean due to spreading on the substrate, the subsequent 39 layers show narrow standard deviations within particular layers (error bars on individual points) as well across many layers (dashed bounding lines on either side of the solid, mean line), with average diameter and deviation given.

FIGS. 3A-F. (A) Digital images depicting that thin 3DG sheets are flexible and can be rolled into more complex 3D forms that may be difficult to 3D print directly. (B) Quasi-static tensile measurements of pure 3D printed PLG, 3D printed PLG-graphene composites, and cast 60 vol. % graphene composite. (C) Corresponding elastic moduli obtained from tensile results and average percent strain to failure for each sample group (n=4), which includes as-printed 60 vol. % graphene (3DG), 100° C. annealed for 30 minutes 3DG, and cast 60 vol. % ink. All groups' moduli and strain to failure are significantly different from each other ($p<<0.05$) except for 60 vol. % and 60 vol. % 100° C. (D) Compression measurement of 75% porous 3DG (60 vol. %) cylinders following annealing at multiple temperatures, illustrating characteristic ductile-to-brittle transition between 100 and 150° C. (E) SEM micrographs of thermally treated 60 vol. % graphene samples, indicating that the particle network does not vary significantly as a function of temperature. (F) Optical images of 60 vol. % cylinders following compression testing, illustrating the brittle failure resulting from annealing above 150° C.

FIGS. 4A-H. (A) Demonstration of electrical conductivity of objects as-printed, showing two 3DG cylinders incorporated into a circuit with a blue LED. (B) Resistivity and normalized volume of 200 µm printed 3DG fibers as a function of annealing temperature (dotted vertical line represents boundary between plastic and brittle behavior). (C) Resistivity of graphene fibers along the fiber direction for various diameter extrusion tips, before and after annealing at 100° C. for 30 minutes in air; the observed diameter-dependent resistivity may be correlated with increased flake alignment for small-diameter extrusion tips. (D) Conductivity of non-annealed fiber extruded from a 400 µm diameter tip, measured along fiber direction, as a function of graphene loading. (E) Electrical resistance of a 400 µm diameter 3DG fiber as a function of tensile strain. As the fiber is strained, resistance increases. This is likely due to increased spatial separation and reduced contact of graphene flakes within the composite, disrupting the continuous graphene network. (F) Resistance of printed graphene fibers on a PEN substrate over 1000 bending cycles to a radius of curvature of 6.5 mm, showing an irreversible resistance increase for large diameter fibers corresponding to buckling deformation with inset images of large-diameter graphene fibers prior to bending and following 1000 bending cycles. (G,H) SEM micrographs of fiber-fiber junctions 3D printed with a 100 µm diameter tip, showing seamless transition between adjacent 3D printed layers (dotted line in H). Arrows indicate fiber directions. Error bars represent a standard deviation of measurements for 3-7 samples in each case.

FIGS. 6A-K. (A,B) Cross-sectional histological digital images of hematoxylin and eosin (H&E) stained 3DG scaffold section explanted 7 days after initial implantation, in which pink stains indicate cellular membranes and tissue, blue stains show cell nuclei, and black is 3DG. The interior of 3DG scaffolds remains mostly acellular, but a characteristic ECM web is pervasive. (C) Masson's trichrome (MT) stained histological image of explanted 3DG scaffolds 7 days after initial implantation showing that synthesized ECM within 3DG scaffold is primarily comprised of collagen. (Not shown, blue stains for collagen; red for cellular material.) (D) MT stained image showing cells deconstructing 3DG strut towards the exterior of the scaffold 7 days after implantation. (E,F) H&E stained images of 3DG scaffold section 30 days after initial implantation, illustrating comprehensive integration of host tissue with 3DG scaffold. 3DG is also significantly deformed and beginning to degrade at this time. (G) MT histological image of day 30 sample illustrating that the majority of ECM is collagen with high concentrations of cells surrounding 3DG material. (H) MT histological image of day 30 sample showing pervasive vascularization (arrows, and dashed lines), comprehensive collagen network, and cellular organization near 3DG material (dotted line). (I) SEM micrograph illustrating ECM network near 3DG (bounded by dotted line) 7 days after initial implantation. (J) SEM micrograph showing vessel-vein pair near 3DG 30 days after implantation. (K) SEM micrograph of graphene flake (box) found embedded in ECM matrix far from 3DG struts.

FIGS. 7A-I. (A) 3DG (60 vol. % graphene) ink can be rapidly 3D printed into self-supporting tubular structures (140 layers) of (B) various sizes that could serve as custom sized nerve graft conduits. (C,D) Uniaxial, multi-channel nerve guides, with very similar architectures to those reported previously, may also be 3D printed from 3DG inks Uniaxial channels are achieved by significantly reducing the z-spacing of progressive layers. (E) SEM micrograph of multi-channel 3DG nerve conduit with every other layer close to contact (box), minimizing or eliminating pores orthogonal to the major axis of nerve guide. (F) 3DG can be 3D printed into structures comprised of many hundreds of layers, such as this high aspect ratio (24:1) 5 mm diameter hollow tube, which can be cut to size as needed. (G) Digital image of tubular 3DG nerve conduit cut from (F) that was implanted into a human cadaver via longitudinal transection and wrapping around the ulnar nerve (white arrows). The 3DG nerve conduit was then sutured closed along the previously described longitudinal transection (white dotted line) as well as to the surrounding epinerium and nerve tissue (inset, circle). Excess 3DG nerve conduit length was then cut with surgical shears to expose additional nerve tissue. (H) Digitally sliced .STL file of skull and skull cap and (I) digital image of resulting 3D printed 3DG skull and skull cap.

FIGS. 8A-C. Structure retention following annealing and resistance-cross section scaling plot. (A) Digital images of 3DG cylinder after being heated for 30 minutes in air at increasing temperature intervals. Even at 500° C., 3DG maintains its original architecture. (B) As-printed line resistance and cross-sectional area for fibers with various diameter extrusion tips. (C) Log-log plot of measured resistance against cross-sectional area for fibers printed with 100, 200, 400 and 1000 µm extrusion tips. The power law exponent of −0.79 is consistent with bulk conductance with an enhanced conductivity in the region near the surface, attributed to flake alignment at the filament surface.

FIGS. 10A-K. Additional 3DG in vivo results 1. (A) Digital image of female BALB/c mouse several minutes after PLG (circle) and 3DG (circle) scaffolds were subcutaneously implanted. (B) Photograph of cross-section of 3DG scaffolds and surrounding tissues immediately after explantation 7 days after being implanted. (C) SEM micrograph of cross-section of day 7 explanted 3DG in vivo sample. Dotted lines outline 3DG strut boundaries. All additional material is ECM and cells formed by the host mouse. (D) SEM micrograph of representative, circular ECM structure, similar to those observed in histology. These circular structures, both large and (E) small were ubiquitous through 3DG day 7 samples but were not found in PLG samples. (F-H) SEM micrographs of day 30 in vivo 3DG samples. Tissue (F) interacts closely with 3DG which is vascularized with both (G) large vessels (dotted line) and (H) capillaries. (I) H&E histological image of day 30 explanted sample highlighting both vascularization (dotted lines) and graphene degradation through macrophage, possibly multi-cellular giant cell, deconstruction (circle and inset). (J) MT histological image highlighting cells concentrated around 3DG strut breaking it down (yellow arrow points to separated graphene). (K) MT histological images highlighting co-localization of vessels near regions of high cell density surrounding 3DG.

FIGS. 11A-H. Additional 3DG and PLG in vivo results 2. (A-C) Additional SEM micrographs of 3DG and (D-F) PLG scaffolds explanted 30 days after implantation. Gross scaffold-tissue structures are displayed in (A) and (D), material-tissue interactions are highlighted in (B) and (E), and representative ECM structures are illustrated in (C) and (F). (G,H) H&E histological images of cross-sections of 30 day explanted PLG scaffold and tissue. Note that PLG was removed by the xylene required for histological processing.

Figure 1:
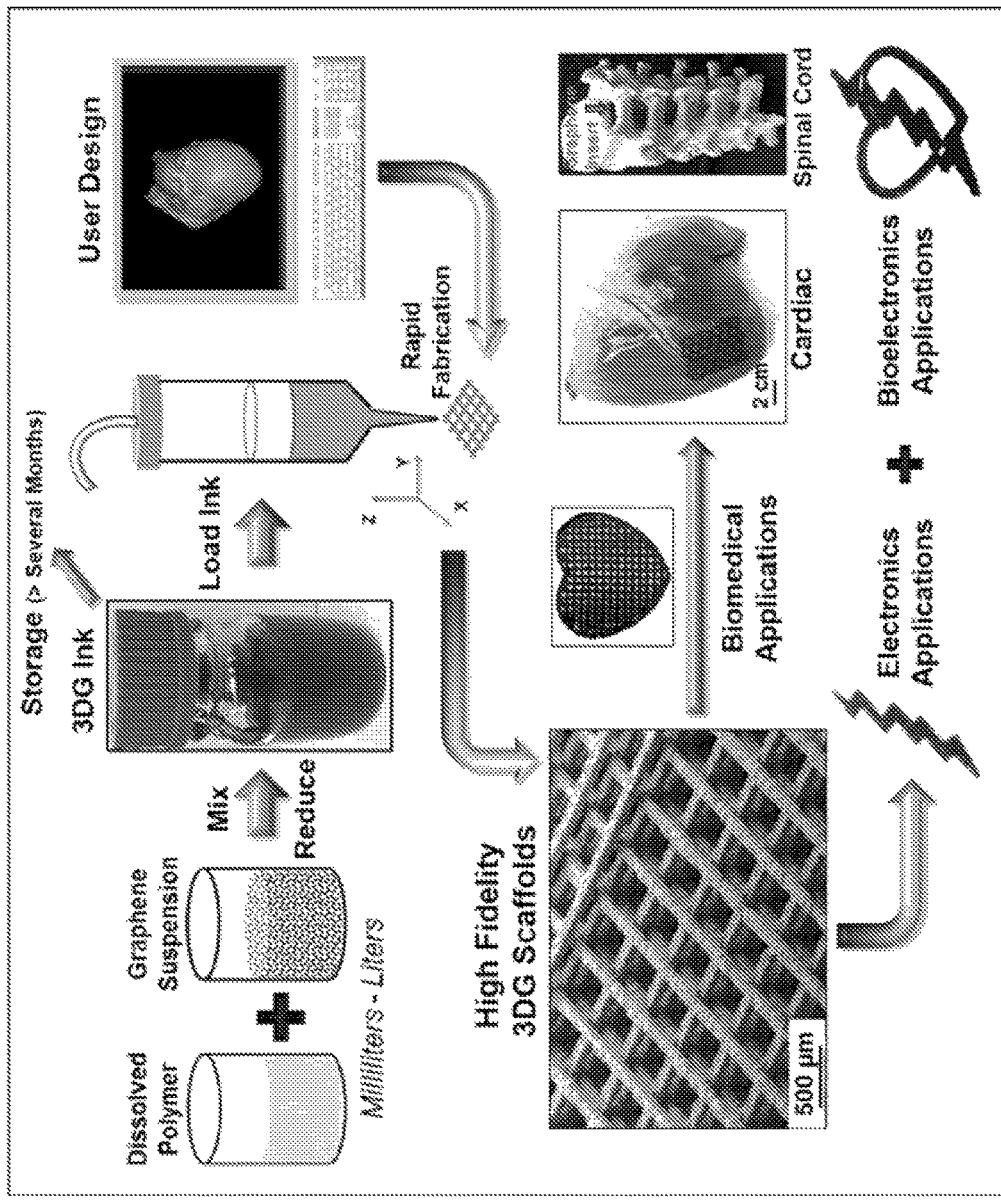
FIG. 1. A schematic illustration of 3DG ink production and 3D printed biomedical articles, in accordance with certain non-limiting embodiments of this invention.

DETAILED DESCRIPTION 3D-printable link compositions comprising graphene flakes and methods of printing the ink compositions into 3D structures, including electrically conductive structures, are provided. Also provided are tissue growth scaffolds made from the inks, methods of forming the tissue growth scaffolds using 3D printing techniques, and methods for growing tissue on the tissue growth scaffolds.

The graphene-based composites that are formed upon printing the ink compositions are electrically conductive, mechanically flexible, biocompatible, and biodegradable. These characteristics enable a range of potential applications in tissue engineering, but also in wearable and implantable electronics, and sensors. Tissue growth and regeneration scaffolds comprising the composites can support the viability, proliferation and/or differentiation of multiple, distinct cell types, including electrogenically bioactive cells. As such, the composites have applications in nerve tissue engineering and regeneration and as single and multi-channel artificial nerve guides.

The ink compositions comprise: a solvent system comprising one or more organic solvents; an elastic organic polymer that is soluble in the solvent system; and graphene flakes. The graphene flakes are thin, planar particles, typically having a thickness no greater than about 100 nm and a longest planar dimension (i.e., width or length) of no greater than about 100 µm. This includes graphene flakes having a thickness of no greater than 50 nm and a longest planar dimension of no greater than 50 µm.

The graphene content in the ink compositions can be varied over a wide range, with a lower graphene content providing a lower electrical conductivity, but greater mechanical flexibility. For example, some embodiments of the ink compositions have a graphene content of at least 20 vol. %, based on the solids content of the ink composition. This includes embodiments of the ink compositions that have a graphene content of at least 40 vol. %, at least 50 vol. %, at least 60 vol. %, at least 65 vol. %, and at least 75 vol. %, based on the solids content of the ink composition.

The elastic organic polymers make up most, or all, of the remainder of the solids content of the ink compositions and the structures made therefrom. Thus, the polymer component of the ink compositions generally provides less than 70 vol. % of the solids content. This includes embodiments of the ink compositions that have an organic polymer content of less than 60 vol. %, less than 50 vol. %, less than 40 vol. %, less than 35 vol. %, and less than 25 vol. %, based on the solids content of the ink compositions.

The elastic polymers provide a binder that helps to hold the graphene flakes together in the final printed structures. The elastic polymers are characterized by the property of elasticity. The elastic polymers should be soluble or substantially soluble in the solvent system at the intended printing temperature. For ink compositions for use in the fabrication of tissue growth scaffolds or implantable sensors, the elastic polymer binders should be biodegradable and biocompatible elastic polymers. In addition, for ink compositions for use in the fabrication of electrogenic tissue growth scaffolds, the elastic polymer binders should be electrically conductive. The elastic polymer may comprise, for example, a polyester, a polymethacrylate, a polyacrylate, a polyethylene glycol, or a combination of two or more thereof. Examples of suitable polyester polymers that can be included in the ink compositions are polylactic acid (PLA), glycolic acid, copolymers of PLA and glycolic acid (i.e., polylactic-co-glycolic acid (PLGA)), and polycaprolactone (PCL). Some embodiments of the ink compositions comprise blends of one or more of these polyesters with other polyesters or with one or more non-polyester elastomeric polymers. Ethyl cellulose is an example of non-biodegradable polymer that can be used.

In addition to the graphene flakes and polymers, the ink compositions may comprise a fluid solvent system comprising a first, primary solvent and at least one other solvent. The solvents should be at least partially miscible, with the first solvent having a vapor pressure greater than the other solvent(s). More specifically, the solvent system may be a graded solvent comprising a primary organic solvent that has a high vapor pressure and, therefore, evaporates rapidly at room temperature and atmospheric pressure (101.3 kPa) and one or more additional organic solvents having lower vapor pressures than the primary solvent at room temperature (23° C.). Suitably high vapor pressures at room temperature and atmospheric pressure include those in the range from about 20 kPa to about 60 kPa, which includes those in the range from about 25 kPa to about 55 kPa.

Some embodiments of the solvent systems comprise dichloromethane (DCM) as a primary solvent, which may be used in combination with the one or more additional organic solvents. The use of DCM is advantageous because, upon extrusion of the ink composition, DCM, which is a very high volatility solvent, evaporates very rapidly, leaving a solid, continuous fiber.

The additional organic solvents desirably have vapor pressures that are lower than that of DCM at the desired printing or deposition temperature (e.g., room temperature—about 23° C.). As a result, the additional organic solvents evaporate more slowly over time, but permit adjacent layers to merge together during deposition, resulting in a single, monolithic structure with strong interlayer adhesion and fidelity. Some embodiments of the solvent systems comprise an additional solvent that is a surfactant, an additional solvent that is a plasticizer, or a combination of at least two additional solvents—one of which is a surfactant and the other of which is a plasticizer. The surfactants prevent or reduce the agglomeration of the graphene flakes, while the plasticizers improve the extrusion properties of the ink compositions. 2-butoxyethanol (2-Bu) (ethylene glycol butyl ether) and dibutylphthalate (DBP) are examples of additional organic solvents that may be included in the solvent system. In solvent systems comprising DBP, the DBP acts as a surfactant. However, other organic surfactants can be used in place of, or in combination with, the DBP. In solvent systems comprising 2-Bu, the 2-Bu acts as a plasticizer. However, other organic plasticizers can be used in place of, or in combination with, the 2-Bu. Some of the ink compositions have solvent systems that consist essentially of, consist of only, a primary solvent, a second solvent that acts as a plasticizer and a third solvent that acts as a surfactant. For example, some of the solvent systems consist of, or consist essentially of, DCM, 2-Bu and DBP. For ink compositions comprising both a plasticizer and a surfactant the preferred mass ratio of the plasticizer to the surfactant will depend, at least in part, on the printing or coating conditions and equipment being used. By way of illustration only, in some embodiments of the solvent systems, the molar ratio of plasticizer to surfactant (e.g., 2-Bu to DBP) is in the range from about 1:1 to about 4:1. This includes embodiments in which the molar ratio is in the range from about 1:2 to about 2:1.

In addition to the ink compositions, structures printed from the ink composition are provided. These structures comprise a solid composite of graphene flakes in a continuous, interconnecting matrix of the organic polymer binder. In part, the present invention can also be directed to the solid graphene composites.

Because the non-solids content of the ink compositions (the solvents) eventually evaporate from structures formed from the ink compositions, the values for the vol. % based on solids content of the ink compositions also reflect the total vol. % for the graphene-based composites made with the ink compositions. Thus, the printed composites can have a graphene content of at least 20 vol. %. This includes embodiments of the composites that have a graphene content of at least 40 vol. %, at least 50 vol. %, at least 60 vol. %, at least 65 vol. %, and at least 75 vol. %.

Fibers printed using the ink compositions can be provided with a filament microstructure, wherein the graphene flakes preferentially oriented along the major (longitudinal) axis of the fiber through the body of the fiber and at the fiber surface. This can be attributed to shear forces experienced by the ink compositions upon extrusion through a print nozzle, or other orifice, that align the graphene flakes along the longitudinal axis of the printed fiber. This is advantageous because the preferential alignment of the flakes along the length of the fiber enhances the electrical conductivity of the fiber. Generally, fibers having a smaller diameter will have a lower resistivity (and, therefore, a higher electrical conductivity). Thus, in some embodiments fibers printed using the ink compositions will have diameter of no greater than 400 μm. This includes embodiments in which the fibers have diameters of no greater than 200 μm and further includes embodiments in which the fibers have diameters of no greater than 100 μm.

Notably, fibers comprising the composites can be electrically conductive as printed. However, an additional post-printing anneal can be used to increase their electrical conductivities. Generally, the anneal should be carried out a temperature of no greater than 100° C. Moreover, the electrical conductivity of the fibers can be maintained even after multiple bending cycles. As a result, the fibers, and scaffolds comprising the fibers, can be used in in vivo tissue engineering applications where natural and external movement of the body can place mechanical strain on implanted objects.

The ink compositions can be used to print objects using a 3D printer and layer-by-layer deposition, where a 3D printer is a printer capable of direct extrusion of an ink composition through a nozzle upon the application of pressure (e.g., via mechanical or pneumatic pressure) to the ink composition, which is held in a container (e.g., a syringe or print head) that is in fluid communication with the nozzle. This type of printing is sometimes referred to as "Direct Ink Writing" (DIW). In some embodiments, the ink compositions are extruded though an opening with a diameter in the range from about 100 microns to about 1 millimeter. However, openings with diameters outside of this range can also be used. The optimal or possible printing rates for the ink compositions will depend on the printing conditions and temperatures and the nature of the object being printed. By way of illustration only, in some embodiments of the printing processes, the ink compositions are printed at rates in the range from 0.1 mm/s to 150 mm/s.

Using the present ink compositions, many layers can be printed in a vertical stack in a layer-by-layer printing technique to form high aspect ratio structures. In some embodiments of the printing methods, arrays of fibers are printed to form each layer, wherein each layer can comprise a plurality of fibers having diameters in the range of, for example, about 100 µm to about 1,000 µm. The vertical stacks can comprise, for example, 10 or more layers, 40 or more layers, 100 or more layers, or 1000 or more layers. Within a layer, the plurality of fibers can be, but are not necessarily, spaced apart and aligned in a substantially parallel arrangement. The fibers in neighboring layers in the vertical stack can be oriented with their longitudinal axes aligned perpendicular with the longitudinal axes of the fibers in a neighboring stack. However, they need not be. Using the present ink compositions, objects can be printed with aspect ratios of at least 5:1, at least 10:1, at least 100:1, at least 1000:1, or even greater, and can have heights of greater than 1 cm, greater than 10 cm, greater than 1 m, or even higher. These high aspect ratios and heights can be achieved in the objects as printed, without the need to fold, roll or otherwise reconfigure a low aspect ratio printed object, such as a planar sheet, after it is printed.

Various three-dimensional articles of manufacture comprising a graphene composite of the sort discussed above, or described elsewhere herein, are provided. Without limitation, such an article can comprise multiple composite components coupled by an ink composition of the present invention. In certain embodiments, such an article can be coupled to, contacting and/or incorporated with viable mammalian cellular material. For example, the ink compositions can be used to print tissue growth scaffolds for tissue engineering applications. Graphene is well suited for such applications because it exhibits electrical conductivity, a characteristic that enhances cell-cell signaling, cell differentiation, and cell function in a variety of cell types, including those comprising muscle, cardiac, and nervous tissues. In addition, the graphene-based composites made from the present ink compositions are flexible and can be formulated with an intrinsic elastic modulus of, for example 3.0±0.4 MPa, which is similar to that of soft tissues, such as spinal cord (1-2.3 MPa).

The tissue growth scaffolds are structures that permit cell adhesion, integration, proliferation, and/or differentiation, as well as tissue ingrowth and vascularization. The graphene-based composites from which the scaffolds are comprised are able to adhere to biological tissues by making contact with them without the need for any adhesives. Because the scaffolds are mechanically flexible and can be printed with a wide variety of shapes and dimensions, they can be designed to be surgically handled, cut, sutured, and manipulated intraoperatively for fine surgical procedures. However, they need not be sutured to stay in place after implantation, as they naturally adhere to biological tissues, without suturing or adhesives. The porosities of the scaffolds can be designed and tailored to optimize cell response and tissue integration for specific applications. By using biocompatible and biodegradable organic polymer binders, the tissue growth scaffolds can themselves be made biocompatible and biodegradable. In addition, because the composites formed by the printed ink compositions are electrically conductive, the tissue growth scaffolds are suitable for use growing electrogenically active tissues, including neurogenically active tissues.

As used herein, the term biocompatible refers to a material or scaffold that does not have a significant negative impact on tissue growth and viability and/or that does not illicit an immune response, such as an inflammatory response, in a living subject (for example a human) into which the material or scaffold is implanted. In addition, biocompatible scaffolds and other implantable devices (such as biosensors) for implantation in a living subject (such as a human) should be infection-resistant. As used herein, the term biodegradable refers to a material or scaffold that can be degraded by biological cells via, for example, hydrolysis. However, for the composites and scaffolds to be considered biodegradable, the graphene flakes need not be degradable, only the polymer matrix.

While the graphene-based ink compositions, the graphene-based composite materials printed therefrom, and the structures form by the composite materials are illustrated by biocompatible and biodegradable, the ink compositions, composite materials, and structures need not be biocompatible or biodegradable and can be used in non-biomedical applications, such as batteries, supercapacitors, solar cells, electronics, heat sinks, and the like. In such applications, the polymer binder can be a non-biocompatible and/or non-biodegradable polymer.

As used herein, the terms electrogenic cells or electrogenic tissues refers to tissues or cells the rely upon or respond to electrical signaling in order to carry out their primary function. Examples of electrogenic cells and tissues include neurogenic cells and tissues (i.e., nerve cells and nervous tissues). Other examples include muscle cells and tissues, such as cardiac cells (e.g., cardiomyocytes) and tissues, and osteo cells and tissues.

The porous scaffolds can be printed via layer-by-layer extrusion of an ink through a print head of a printer, such as a bioplotter (e.g., Envision TEC, GmbH), or through the needle of a syringe. The use of 3D printing for the fabrication of the scaffolds is advantageous because it provides for regular geometric patterning of the layers that make up the scaffold, which makes it possible to control and tailor the porosity, pore size and pore interconnectivity of the scaffold. For example, the printed layers may comprise a plurality of printed fibers, which may be arranged in an ordered three-dimensional grid. In some embodiments of such grids, the fibers in each layer are substantially parallel to one another, while the fibers in a given layer are not oriented parallel to the fibers in other layers. The printing can be carried out at relatively low extrusion temperatures, including temperatures in the range from about room temperature (i.e., ~23° C.) to about 40° C.

The scaffolds can be used to support and direct the generation of electrogenic cells or tissues in vivo by contacting them with electrogenic cells or electrogenic tissue in vivo, whereby electrogenic cell generation takes place on the scaffold. Because the scaffolds are biocompatible, electrogenic cells and tissues that come into contact with the scaffolds retain their viability and can interpenetrate the scaffolds and become vascularized.

The scaffolds can also be used to generate electrogenic cells or tissues by contacting the scaffolds with cells that are capable of differentiating into the desired electrogenic cells, under conditions that promote such differentiation, and allowing the differentiation to occur. Stem cells, including human stem cells, and, in particular, human mesenchymal stem cells, can be used as the cells that are capable of differentiating into the desired electrogenic cells. This process can be carried out in vitro by seeding the scaffolds with the cells and culturing the cell-seeded scaffold in a cell culture medium. Alternatively, this process can be carried out in vivo by implanting the scaffolds into electrogenic tissue in a living being and allowing natural signals from the electrogenic tissue to induce the differentiation of the cells. In such in vivo applications, the scaffolds can be pre-seeded with cells that are capable of differentiating into the desired electrogenic cells prior to implantation in order to facilitate the in vivo growth (including regeneration) of electrogenic cells and/or tissues. Cells that can be used to seed the scaffolds include cell lines, adult stem cells, induced pluripotent derived stem and non-stem cells.

Notably, if the scaffold has a sufficiently high electrical conductivity, neither the scaffolds nor the culture medium need to include any differentiating biochemical factors. By way of illustration, scaffolds comprising at least 60 vol. % graphene flakes, which provides a high electrical conductivity, are able to induce the differentiation of human mesenchymal stem cells into neural cells in the absence of neuronal differentiating biochemical factors factors. Some embodiment of the tissue growth scaffolds consist of only, or consist essentially of, the graphene and the polymeric matrix, prior to be contacted with the electrogenic cells.

Some embodiments of the scaffolds are configured (for example, sized and shaped) to provide a nerve guide. Nerve guides (also referred to as nerve conduits or nerve guidance conduits) are conduits that provide a guided pathway from one nerve/nerve bundle end to another nerve/nerve bundle end. Or, to provide a guided pathway to connect a nerve/nerve bundle end to other biological tissue, such as neurogenic tissue in a living subject. Such nerve guides are used to provide physical guidance for nerve regeneration for severed or otherwise damaged nerves. As the severed or damaged nerves grow/regenerate, they preferentially follow the direction of the nerve guide conduits.

The tissue growth scaffolds can also be used to grow biological tissue from mature biological cells in vitro by seeding the scaffolds with biological cells and culturing the cell-seeded scaffolds in an appropriate culture medium, under conditions that promote cell proliferation. Because the scaffolds are electrically conductive, cells that require electrical stimulation in order to proliferate, such as certain osteo cells, can be cultured using the scaffolds.

In addition to applications in tissue engineering, the scaffolds can be used for the study of the response of cells to electrical stimuli by seeding the scaffolds with biological cells, which may be electrogenic cells, sending a current through the scaffold, and monitoring the response of the biological cells to the applied current. The scaffolds can also provide tissue growth guides for other severed, or otherwise damaged, biological tissues. For example, a scaffold can be implanted such that is connects first segment of muscle tissue to a second segment of muscle tissue in the living being, wherein the scaffold acts as a tissue growth guide by directing muscle tissue generation along its length The scaffolds also find applications in implantable biosensors.

EXAMPLE

The following non-limiting example and data illustrate various aspects and features relating to the compositions, composites, articles and/or methods of the present invention, including the preparation of various biomedical articles, structures and scaffolds, as are available through use of the graphene ink compositions and related composites described herein. In comparison with the prior art, the present compositions, composites and articles/structures provide results and data which are surprising, unexpected and contrary thereto. While the utility of this invention is illustrated through the use of several articles/structures, graphene ink compositions and associated components, it will be understood by those skilled in the art that comparable results are obtainable with various other articles/structures, ink compositions and components thereof, as are commensurate with the scope of this invention.

As relates to certain non-limiting embodiments of this invention, 3D printable graphene inks can be used to provide electrically conductive, mechanically resilient, and biocompatible scaffolds with high graphene content (e.g., 60 vol. % or more solids loading). Such a solvent-based 3D graphene (3DG) ink is comprised of graphene flakes and the biocompatible, biodegradable, and hyperelastic polyester polylactide-co-glycolide (PLG). 3DG can be printed at room temperature via extrusion into self-supporting, user-defined structures with fidelity and precision. The resulting majority-graphene structures are mechanically robust and plastic in nature, with thin constructs displaying a high degree of flexibility. Furthermore, the 3DG presented here exhibits improved electrical conductivity compared to previously-reported 3D printed carbon-based materials. Such constructs can be used as electrically conducting scaffolds for tissue regenerative engineering applications, as demonstrated using in vitro and in vivo biocompatibility studies. Overall, such 3DG inks enable rapid fabrication of 3D graphene objects with novel and desirable mechanical, electrical, biological, and handling properties. Additionally, simple and scalable ink preparation, along with room temperature 3D printing, enable versatile design and fabrication of graphene objects with additional potential applications in medicine, bioelectronics, sensors, and energy devices (FIG. 1).

Representative of certain embodiments, a 3DG ink was prepared from commercially available materials using standard mixing of components followed by solvent evaporation, all performed under ambient conditions. The ease of preparation of this ink and its long shelf life of at least several months render it a highly scalable procedure. To prepare the graphene-based inks, PLG is first dissolved in dichloromethane (DCM), a high vapor pressure solvent. Separately, graphene powder [3-8 atomic layers thick, 3:2 (60 vol. % or ~75 wt. % graphene; 3DG), 2:3 (40 vol. % or ~56 wt. % graphene), and 1:4 (20 vol. % or ~32 wt. % graphene) by volume graphene:PLG, corresponding to approximately 3:1, 3:2, and 3:7 by weight, respectively] is dispersed in a mixture of DCM and smaller relative volumes of 2-butoxyethanol, a surfactant, and dibutyl phthalate, an effective plasticizer. DCM is initially added in excess to permit easy mixing and dispersion of components. The PLG solution and graphene dispersion are combined and thoroughly mixed by hand, vortexing, or rocking until homogeneous. Over the course of several hours (dependent on total ink volume), excess DCM evaporates while open in a sonicating bath until a quasi-static shear rate viscosity of approximately 30 Pa·s is achieved. At this point, the 3DG ink may be stored in a well-sealed glass container under refrigeration prior to use. The shear-thinning nature of the ink, combined with the graded volatility of the solvents, allows for room temperature extrusion-based printing to produce self-supporting structures.

Figure 2E:
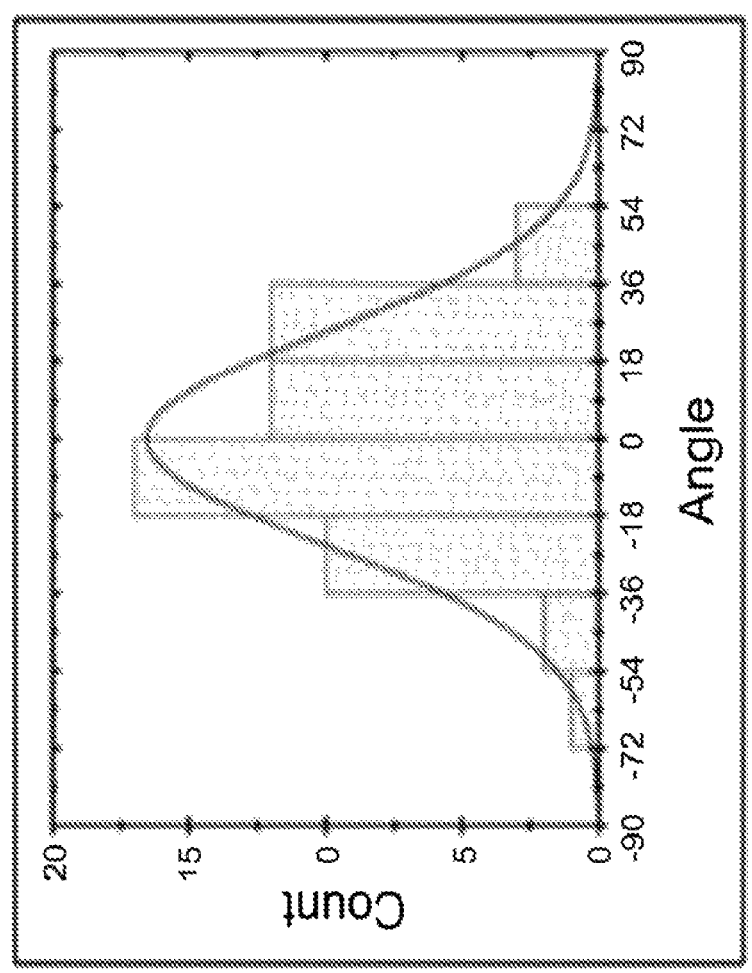
Figure 2F:
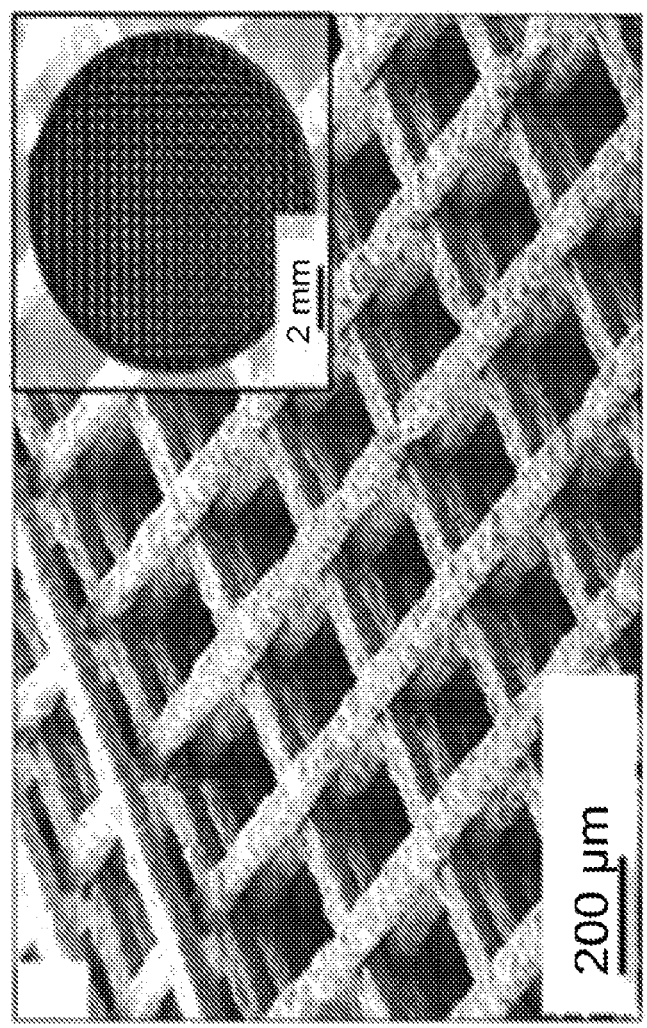
Figure 2G:
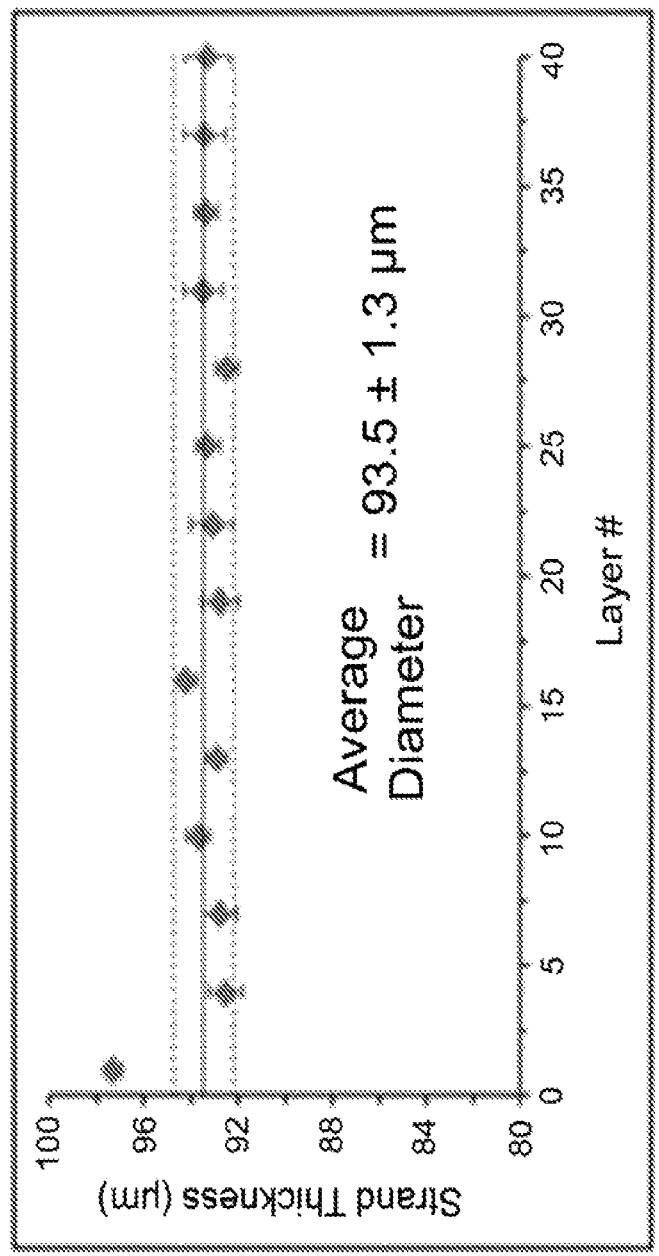

When printing 3DG, which is comprised of 60 vol. % graphene and 40 vol. % PLG (corresponding to 75 wt. % graphene, 25 wt. % PLG), the 2D nature of the graphene particles and the uniaxial nature of the printing process couple to produce objects with anisotropic microstructure and properties. The 3DG ink is a relatively viscous dispersion of randomly oriented graphene particles suspended in a dissolved elastomer solution. Upon extrusion (FIG. 2A), resulting shear forces promote reorientation and alignment of the flakes along the direction of flow. The net effect is a filament microstructure with flakes oriented along the fiber surface (FIG. 2B-E). This is distinct from samples cast from the ink, which exhibit more random orientation. The elastomer is present in sufficient quantities to form a continuous, interconnecting matrix between the graphene flakes. Rapid evaporation of the DCM solvent following extrusion is critical to create self-supporting fibers that do not significantly deform following deposition (FIG. 2F). Under ambient conditions, DCM has a vapor pressure exceeding 50 kPa, roughly nine times that of pure ethanol under the same conditions (5.5 kPa). The high vapor pressure of DCM, combined with the high surface area to volume ratio of extruded material, results in rapid evaporation of DCM, producing self-supporting fibers upon extrusion. The presence of the remaining low vapor pressure solvents, 2-butoxyethanol (0.1 kPa) and dibutyl phthalate ($9 \times 10^{-6}$ kPa) impart enough liquidity to the deposited material to enable seamless merging of subsequent 3D printed layers resulting in physically smooth transitions between adjacent layers, a common challenge for direct ink written 3D printing technologies. The result of this process is a 3DG ink that can be extruded from tip diameters as small as 100 μm and at speeds greater than 150 mm/s to produce highly uniform, multi-layered structures (FIG. 2F). Detailed characterization reveals that individual strands comprising the structure are approximately 6% smaller than the tip diameter, providing evidence of volume reduction during drying. In addition, the dimensions of printed fibers are consistent both within a single layer and across dozens of layers, with an average strand thickness among 120 measured strands deviating only 1.4% from the mean (FIG. 2G).

Figure 3A:
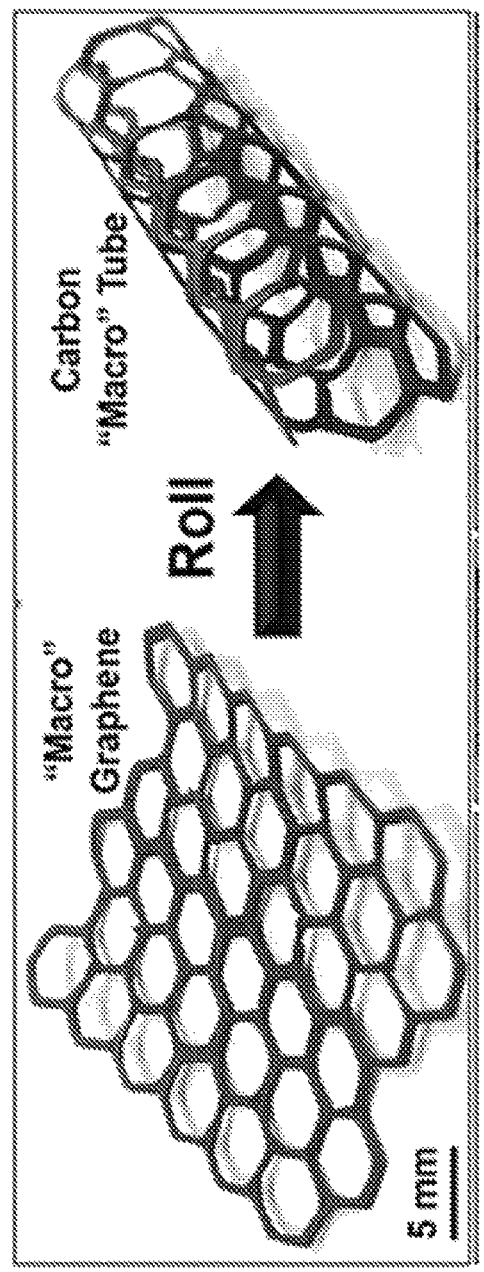
Figure 3B:
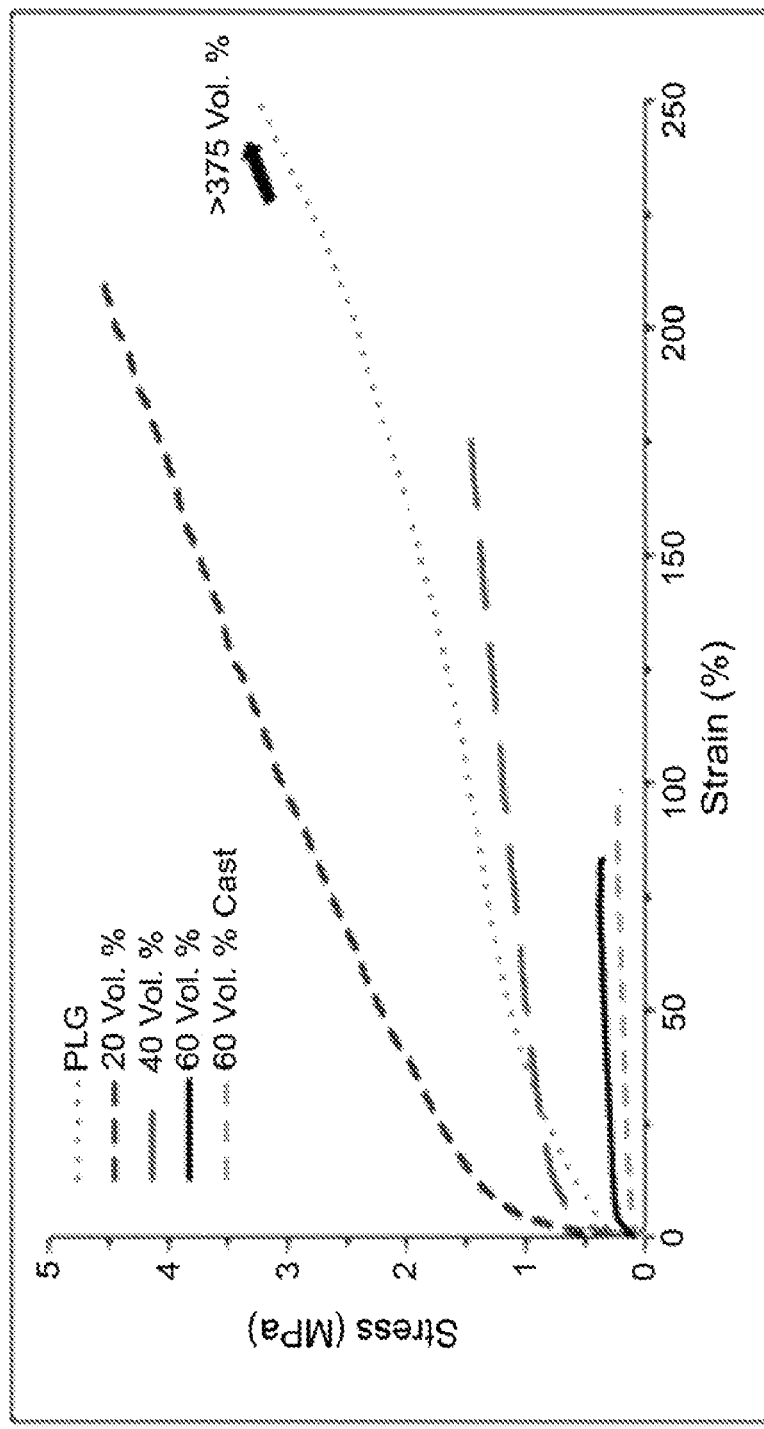

Despite its high particle content, the graphene-polymer composite is mechanically stable and versatile. The unique properties of 3DG enable thinner printed structures to be rolled, folded, cut, and even fused together using 3DG ink. In this manner, a complex 2D geometric hexagonal array can be rolled by hand to form a 3D object, such as a carbon "macrotube" (FIG. 3A). The flexible nature of these printed objects is attributed to the specific choice of PLG as the polymer binder. To more quantitatively assess the mechanical behavior of the 3DG system and composites with lower graphene loading, tensile and compressive properties of the 3D printed constructs were tested. Although not nearly as elastic as their pure PLG counterpart, 3D printed graphene-PLG composites can be strained to greater than 210% for 20 vol. % (of solid) graphene loading and 81% for 60 vol. % graphene loading prior to failure (FIG. 3B). As expected, strain-to-failure is inversely proportional to graphene loading. However, the elastic modulus, although initially increased over pure PLG for 20 vol. % graphene, decreases significantly with increased graphene content (FIG. 3C), ultimately resulting in a modulus of 3 MPa for 3DG (60 vol. % graphene), perhaps due to the fact that tensile loads are primarily carried by the PLG elastomer. As graphene content increases towards and beyond 40 vol. %, PLG is unable to sufficiently coat and tightly bond neighboring graphene particles, decreasing both the strength and elastic moduli of the high graphene content composites. Note that cast 60 vol. % graphene samples were approximately three times stiffer than their 3DG counterparts (FIG. 3C), a variance that may stem from differences in flake orientation and material porosity. Because they can slip past each other, aligned flakes in the 3D printed constructs require less force to translate along a parallel direction of loading. In the cast system, flakes are more randomly oriented in a manner that inhibits slip upon loading, resulting in an increased elastic modulus. Interestingly, the shape of the graphene flakes contributes significantly to the stability and flexibility of the resulting 3D printed structures. Other carbon-based nanoparticles, such as aggregated carbon nanotubes formed into inks and printed in the same manner as 3DG, result in structures that are exceptionally brittle and fracture after minimal handling. In this latter case, the dense, micron-scale clusters of carbon nanotubes cannot translate upon loading, resulting in brittle fracture. Under compressive loads, 3DG cylinders display typical plastic foam behavior (FIG. 3D). These tensile and compressive properties are maintained even when samples are annealed in air up to 100° C., but deteriorate rapidly at temperatures equal to or exceeding 150° C. (FIG. 3D) due to PLG decomposition. Although inspection of the various microstructures (FIG. 3E) does not reveal a significant variation between samples annealed at the different temperatures, structures heated above 150° C. undergo brittle failure upon compression (FIG. 3F).

Open-mesh cylinders fabricated from 3DG support electrical current as-printed, as illustrated by an activated LED in series with the 3DG cylinders (FIG. 4A). Resistivity measurements of as-printed 3DG fibers verify their electrical conductivity (FIG. 4B). Annealing in air up to 500° C. leads to no noticeable volume change in fibers or 3D printed porous cylinders (FIG. 8A); however, the resistivity measured along the fiber length decreases to 0.114±0.002 Ω·cm (conductivity of approximately 875 S/m) when structures are annealed in air at 100° C. This resistivity represents an order of magnitude improvement over previously reported carbon-based 3D conductive inks. The conductivity of 3DG along the fiber direction is inversely dependent on the diameter of the extrusion tip, with small-diameter (<400 μm) extrusion tips corresponding to lower resistivity (FIG. 4C). This difference is likely associated with the microstructure of the extruded filament. Fibers extruded from small-diameter tips experience a higher shear rate during extrusion, facilitating more complete alignment of the graphene flakes. Additionally, small-diameter fibers exhibit a higher surface-to-bulk ratio, enhancing the effect of particle alignment at the surface. The filament resistance scales with the cross sectional area (FIG. 8B) according to a power-law relationship having an exponent of −0.79±0.03, which is intermediate between bulk and surface conduction exponents of −1 and −0.5, respectively (FIG. 8C), indicating enhanced electrical conductivity along the surface. This corresponds well with the description of shear-induced flake alignment, as well as previously reported electrical effects of graphene alignment, as the shear rate is significantly higher at the fiber surface due to the confined flow geometry and the shear-thinning nature of the ink. In general, the shear alignment of graphene flakes during extrusion, supported by both morphological and electrical characterization, offers a compelling foundation for the alignment of other anisotropic nanomaterials to more precisely tailor the properties of 3D printed objects.

Figure 3C:
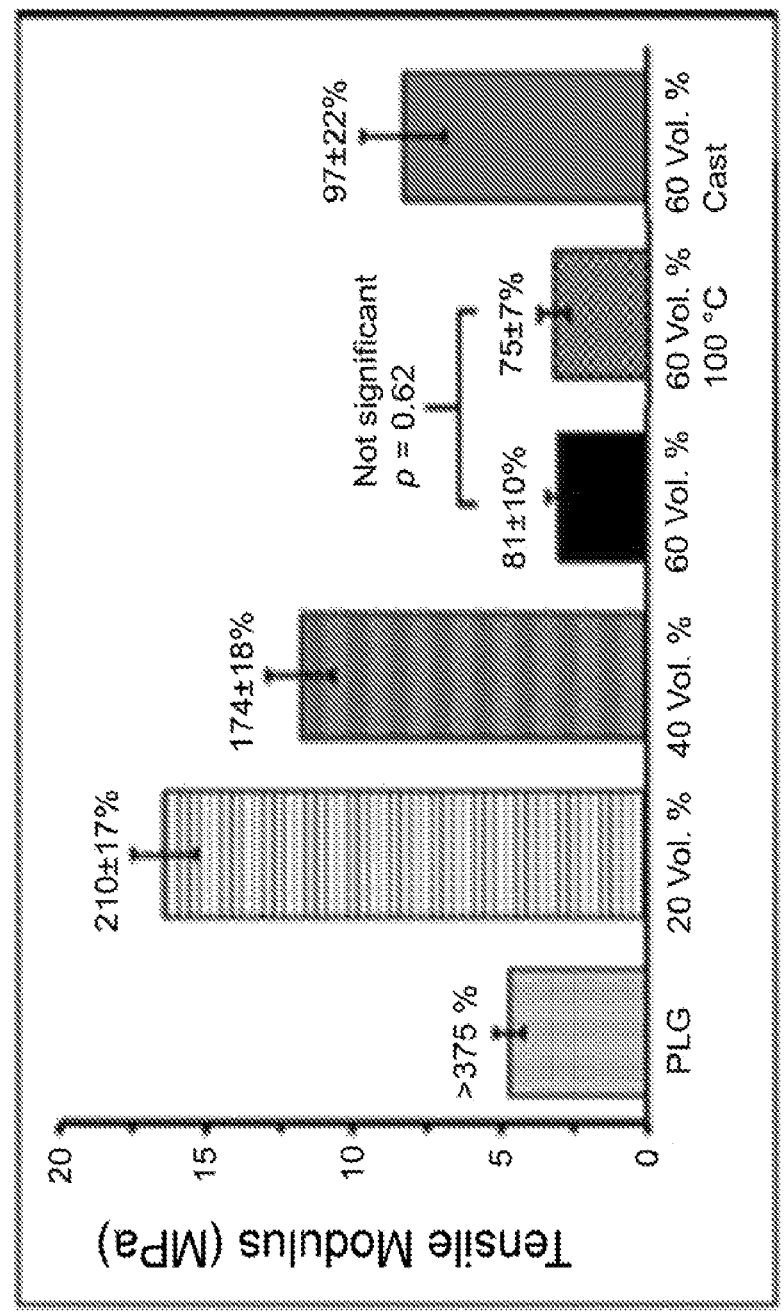

The electrical properties of the material are also dependent on graphene loading (FIG. 4D). Even a lower loading of 20 vol. % graphene results in appreciable conductivity. While exhibiting a lower electrical conductivity, these lower graphene content composites are significantly stiffer and can undergo three times more strain prior to failure than the 3D printed 60 vol. % graphene composites (FIG. 3B-C). This range of mechanical and electrical properties indicates the potential to tailor the 3D printed graphene system to specific applications by simply altering the particle content in the initial inks.

Because 3DG exhibits flexibility and mechanical tolerance, its electrical properties under mechanical deformation were also evaluated. Resistance increases by a factor of approximately 10 for 400 µm fibers strained up to 20% (FIG. 4E), likely resulting from the reduced points of contact between individual graphene particles as the elastomer is strained around them. In contrast, under cyclic loading to small strains (experienced during bending) the conductivity is maintained, indicating the reversibility of the deformation. 3DG filaments were printed onto a 50 µm thick polyethylene naphthalate (PEN) film for handling. FIG. 4F presents the evolution of the line resistance for fibers of 100, 200, 400, and 1000 µm tip diameter over 1000 bending cycles to a radius of curvature of 6.5 mm. In this measurement design, the entire fiber is under tension during flexing. While the small-diameter fibers exhibit little variation in resistance, the large diameter fibers undergo an irreversible deformation (FIG. 4F, lower inset), which corresponds to an increase in resistance by a factor of 1.68±0.04. This ability for small diameter fibers to maintain mechanical integrity and electrical conductivity through many bending cycles is beneficial for in vivo tissue engineering applications where natural internal and external movement of the body are likely to place mechanical strain on the implanted objects.

Figure 4H:
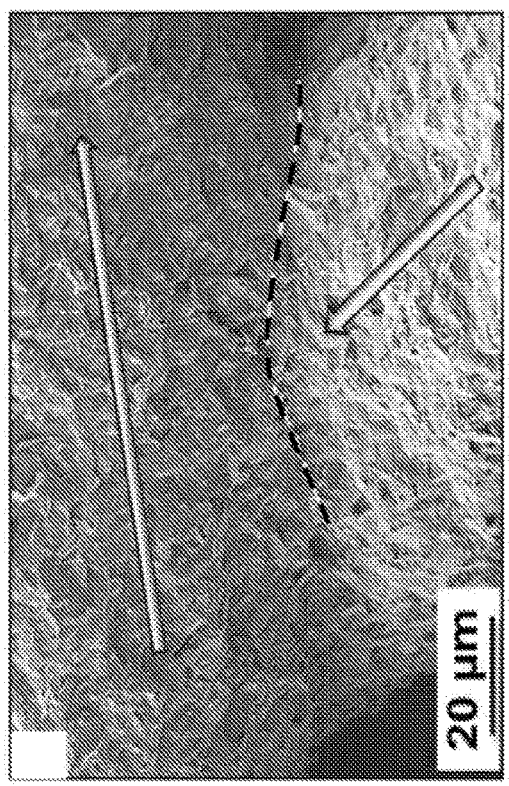
Figure 4G:
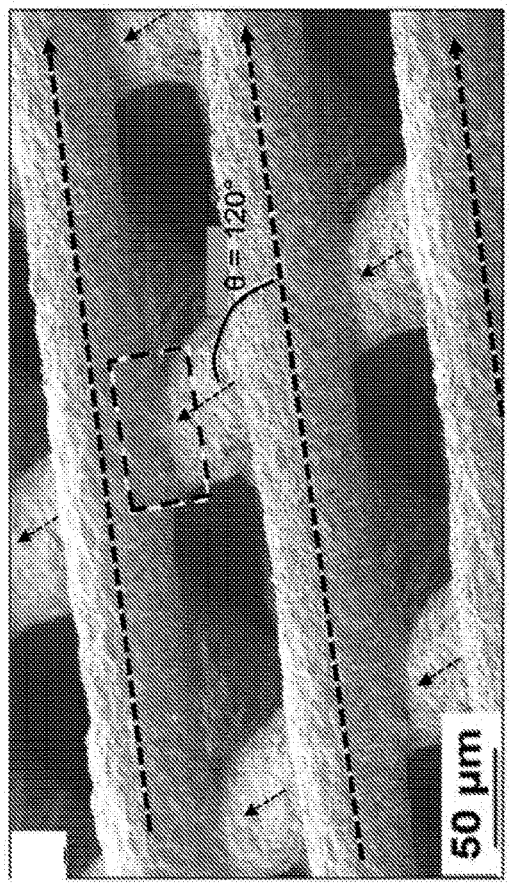

While the results thus far correspond to single printed fibers, with resistance measurements taken along the printing direction, 3D printed structures contain networks of connected fibers. In such complex structures, the junctions between fibers can dominate the electrical properties of the system. As shown in FIGS. 4G and 4H, the junctions between two subsequent layers of graphene are characterized by smooth, seamless transitions due to the solvent evaporation dynamics of the system, which enable adjacent layers to seamlessly fuse together while retaining their structural integrity. Measurements of the absolute resistance associated with this junction indicate a value below the measurement variability of approximately 10Ω, indicating excellent layer-to-layer fusion.

To determine if 3DG can support cell viability and proliferation, and whether or not it can influence stem cell fate, female bone marrow-derived human mesenchymal stem cells (hMSCs) were statically seeded onto 4 mm-diameter 3D printed scaffolds containing 60 vol. % graphene (3DG), 20 vol. % graphene, and pure 3D printed PLG.

Figure 5A:
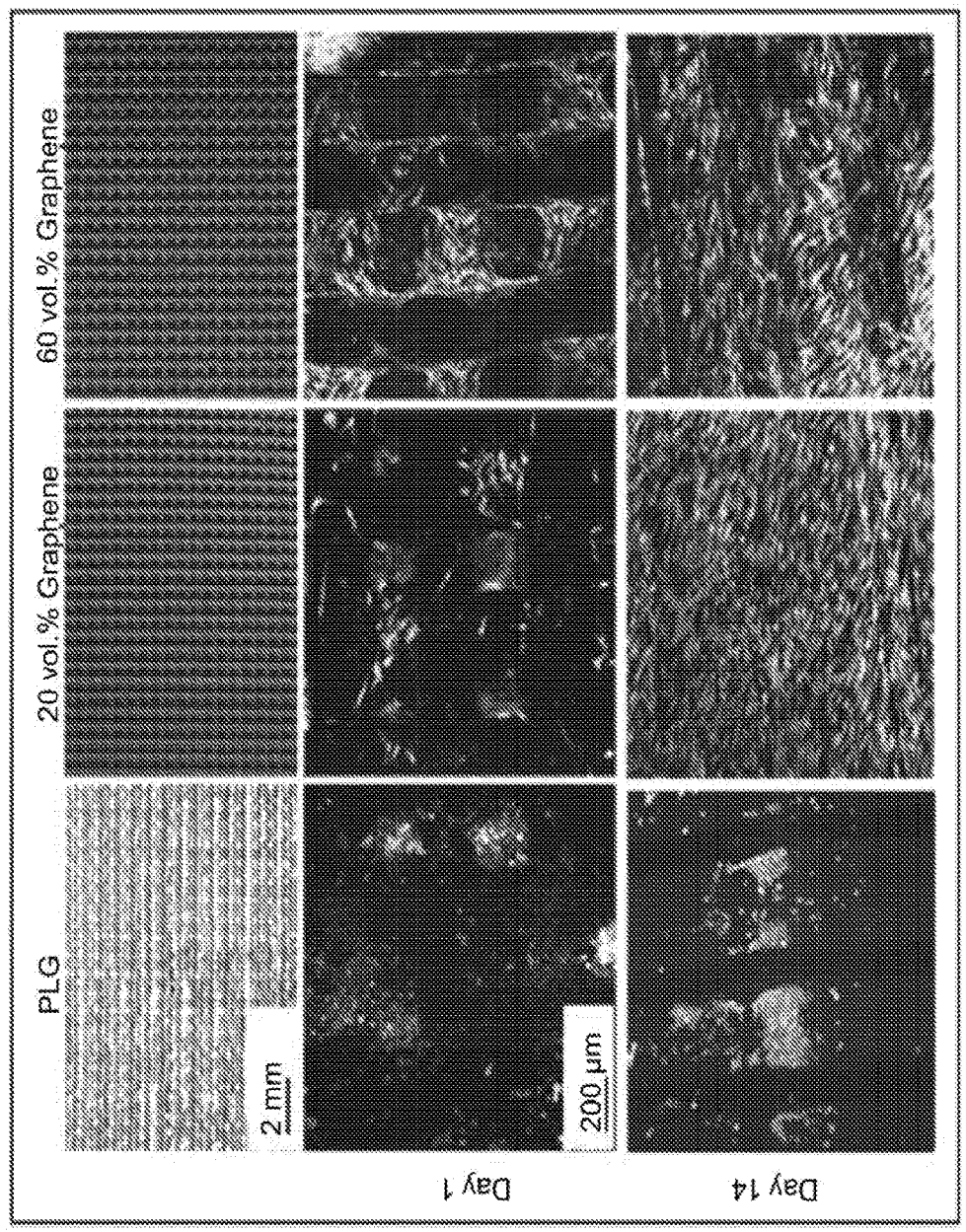
FIGS. 5A-H. (A) Digital images (top row) and scanning laser confocal 3D-reconstruction projections of live stained and dead stained hMSCs on various scaffolds 1, 7, and 14 days after being seeded. (B) Number of hMSCs present on scaffolds (n=3) as a function of material and days after seeding as determined from DNA quantification. Dotted line represents initial cell seeding number (50,000). (C) Neurogenic relevant gene expression of cells on 20 and 60 vol. % graphene 7 and 14 days after being seeded normalized to expression of day 0, unseeded hMSCs. * represents significant ($p<0.05$ day 14) increase over same material group and same gene at day 7. ** signifies significant ($p<0.05$) difference between indicated material groups (n=4). SEM micrographs of hMSCs on (E) 20 and (E) 60 vol. % graphene scaffolds 7 days after being seeded. (F) Higher magnification SEM micrograph of cells on day 7, 60 vol. % graphene scaffolds, showing hMSC connecting via a small segment of a long, "intercellular" wire. (G) Scanning laser confocal 3D-reconstruction of live and dead cells on day 14 for 60 vol. % graphene scaffolds and (H) detail of cell indicated by arrow in (F). For panels (B) and (C), * indicates significance of $p<0.05$ between compared groups (n=4); ** indicates significant ($p<0.05$) difference over previous time point for the same material group.
Figure 5B:
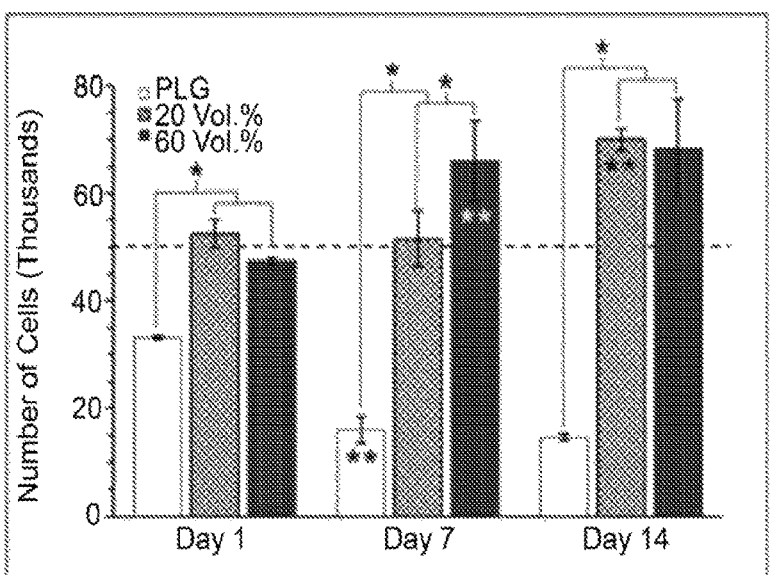
Figure 5C:
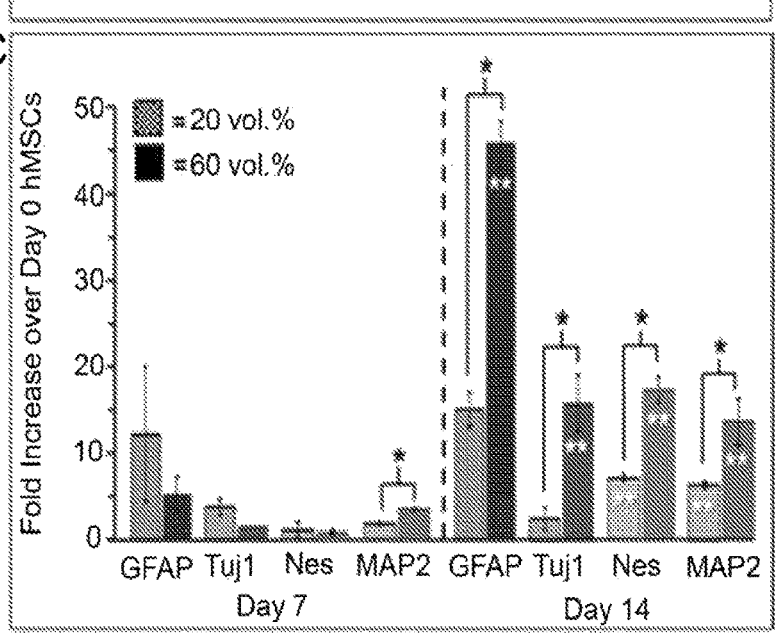
Figures 5D, 5E:
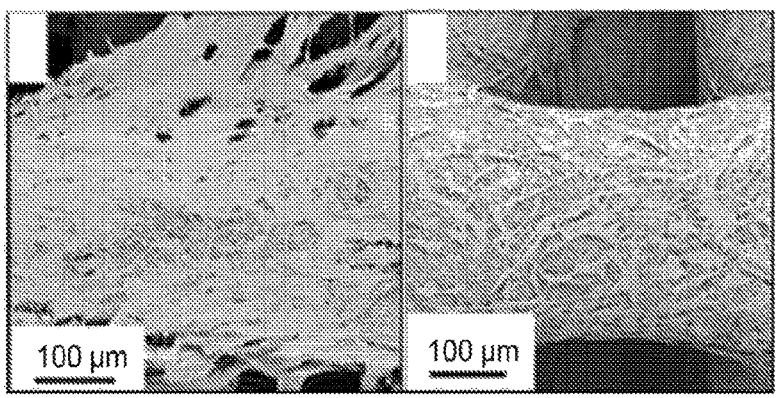
Figure 5G:
Figure 5F:
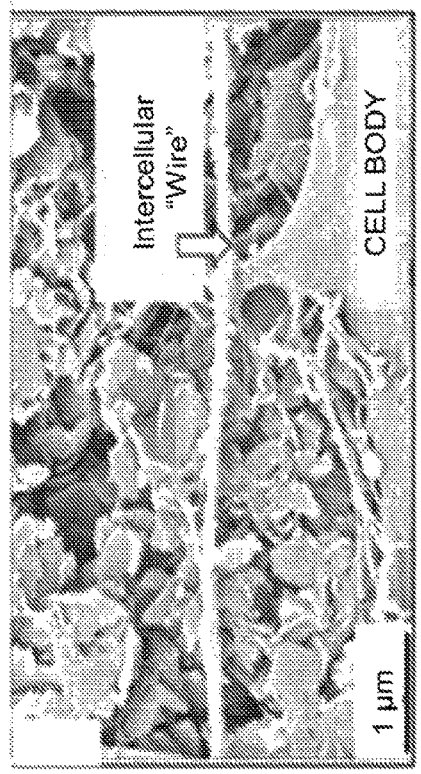
Figure 5H:
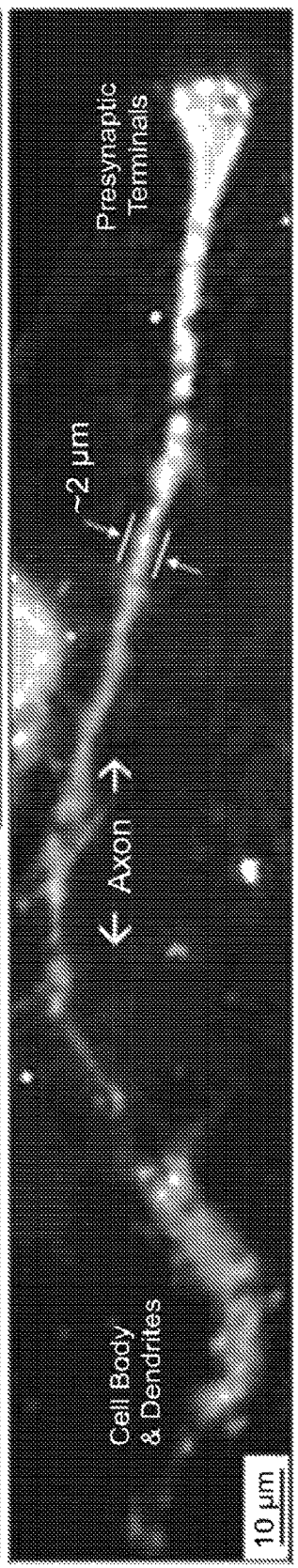

Over the course of two weeks, in standard DMEM growth medium, hMSCs remain viable on 20 and 60 vol. % graphene scaffolds (FIG. 5A) and proliferate (FIG. 5B) to coat individual struts and span the inter-strut gaps. Viability and proliferation on PLG using the same solvent-based room temperature printing method was significantly lower relative to the graphene-containing scaffolds. This difference could be due to a number of variables including surface roughness, mechanical properties, and electrical conductivity. Both 20 and 60 vol. % graphene scaffolds supported hMSC viability and proliferation to a similar degree; however, significant variations in phenotypic response were observed by day 14. Glial and neurogenic relevant genes, glial fibrillary acidic protein (GFAP), neuron-specific class III ß-tubulin (Tuj1), nestin (Nes), and microtubule associated protein 2 (MAP2) are upregulated in cells on both the 20 and 60 vol. % graphene scaffolds over the course of two weeks relative to initial expression of unseeded day 0 hMSCs (FIG. 5C). By day 14, however, cells on 60 vol. % graphene exhibit 6, 3, 2.5, and 2 times greater expression of GFAP, TujI, Nes, and MAP2 respectively, compared to cells on the 20 vol. % graphene scaffolds. There is also a distinct difference in cell morphology at this time, where hMSCs on 20 vol. % graphene exhibit a confluent sheet-like morphology (FIG. 5D), which is characteristic of adherent cell types such as fibroblasts and similar hMSC lineages. In contrast, hMSCs on 60 vol. % graphene develop into highly elongated morphologies and do not form confluent sheets (FIG. 5E). Instead, high aspect ratio cellular extensions (often greater than 100 µm in length) are found throughout the 60 vol. % graphene scaffolds, connecting individual cells through "wire-like" networks (FIG. 5F). Closer inspection of cells on day 14 (FIG. 5G) illustrate that a segment of the population exhibits morphologies similar to uni- or multi-polar neurons, including approximately 2 µm-diameter axon-like extensions, consistent with those of unmyelinated axons as well as features that resemble presynaptic terminals (FIG. 5H).

Figures 9A, 9B:
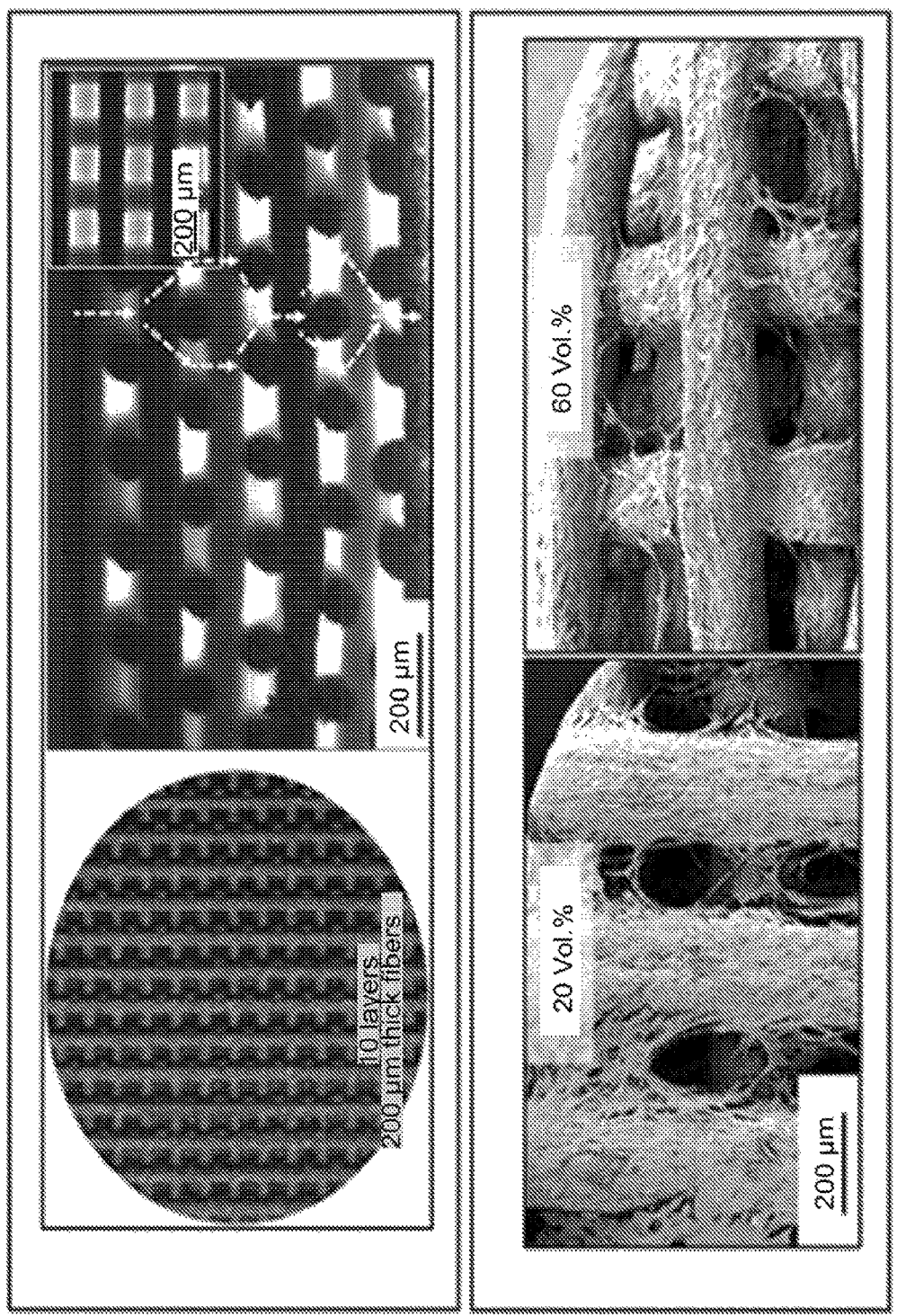
FIGS. 9A-D. Additional in vitro imaging, including Cardiomyocyte and iNeuron adhesion on 3DG. (A) Top-down photograph and corresponding cross-sectional image (inset) of 0-90° offset scaffold design utilized for in vitro studies. Dotted white arrows show example of tortuous pathway seeded cells could follow upon seeding, increasing chances of cell-to-scaffold adhesion and increasing seeding efficiency. (B) SEM micrographs of hMSCs on 20 and 60 vol. % graphene scaffolds 7 days after being seeded. (C) SEM micrographs of rat cardiomyocytes and human induced pluripotent stem cell derived neurons on 3DG scaffold 1 week after being seeded. Top row displays low magnification images illustrating attachment of multiple cells on 3DG surface. Bottom row displays high magnification images of single cell interactions with underlying 3DG. (D) SEM images of 20 and 60 vol. % graphene scaffold cross-sections 14 days after seeding with hMSCs. hMSCs can be seen coating (yellow arrows indicate several regions with cells for reference) the struts throughout the thickness of the scaffolds as well as bridging layers.
Figure 9C:
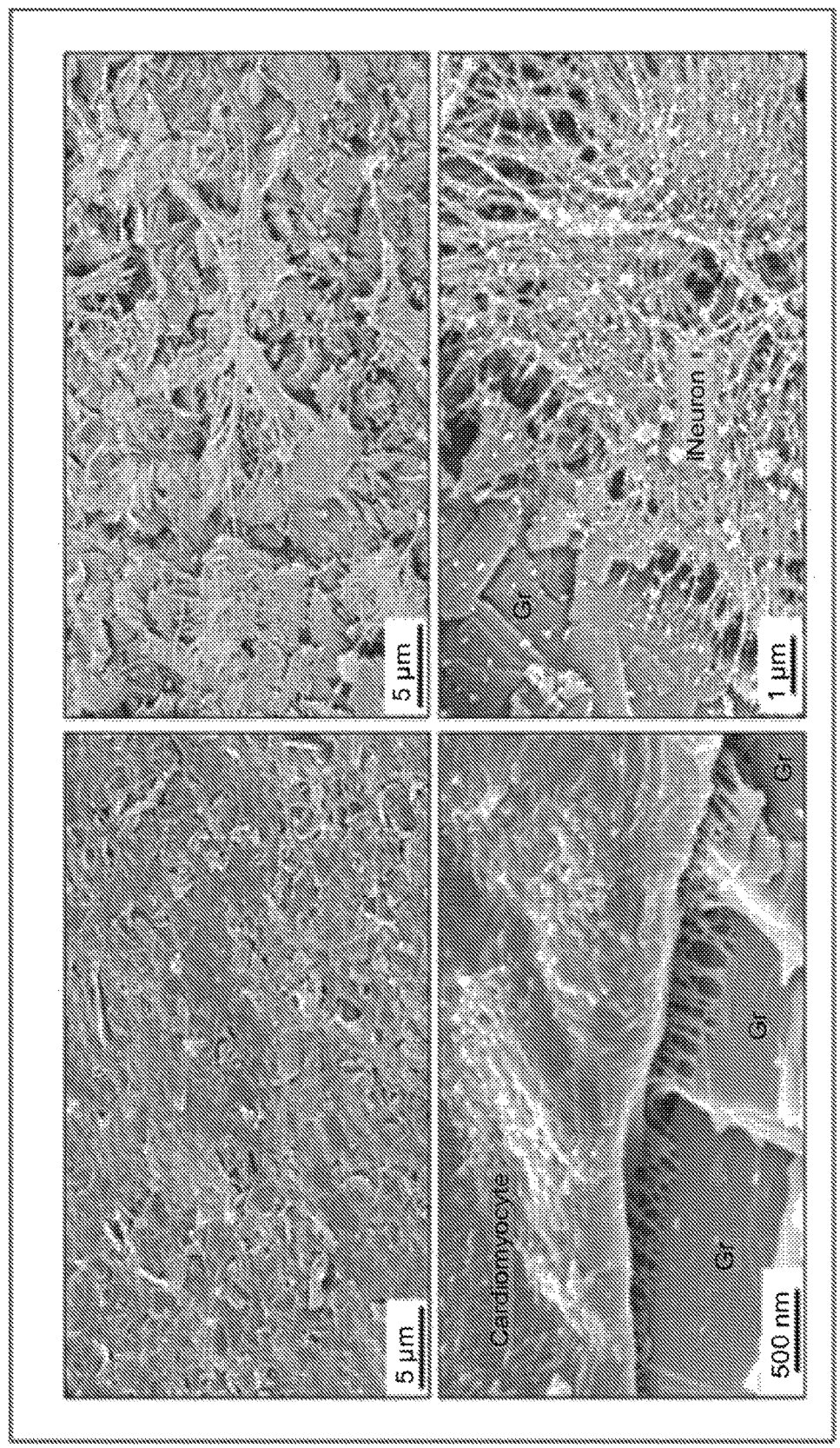
Figure 9D:
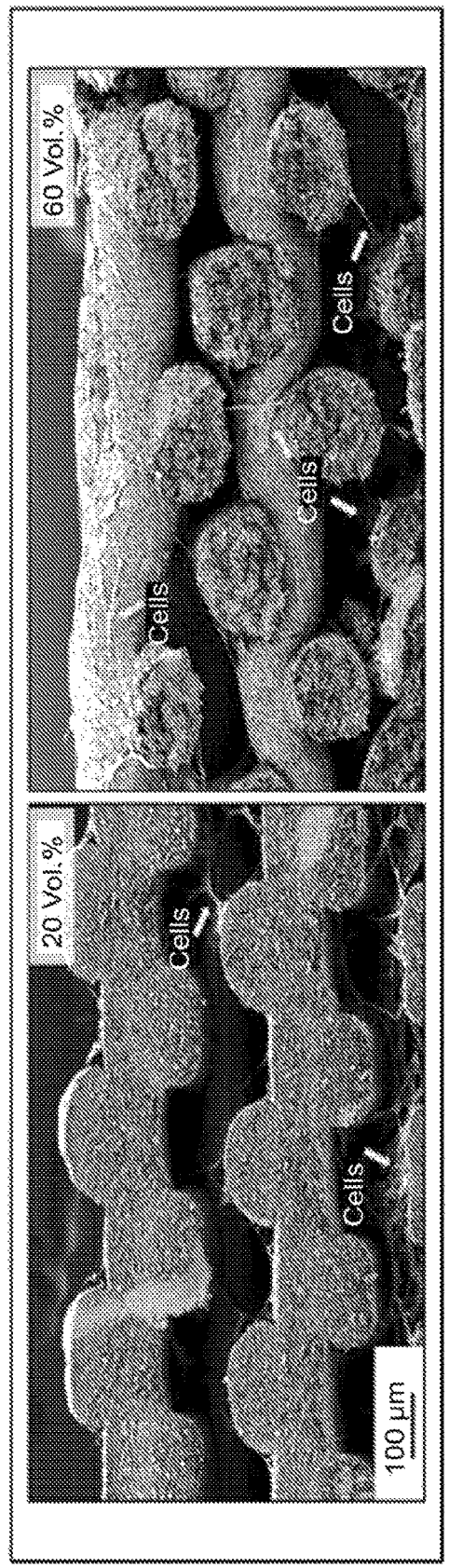

While there is ample evidence that neuronal stem cell (NSC) function and differentiation can be aided in the presence of graphene and graphene oxide modified substrates and foams, there is less work illustrating that hMSCs cultured under similar conditions, in the presence of graphene, can differentiate and become neuron-like. The few existing studies that do demonstrate this potential, however, show that hMSC differentiation into neuron-like cells is possible when cultured in medium containing neuronal-inducing chemical and biological factors, such as retinoic acid, bFGF, and BDNF. It is shown here, however, that with elevated graphene concentrations presented by 3DG, exogenous factors may not be required to induce neurogenic differentiation of hMSCs, demonstrating its inherent neuronal-inducing capabilities. These results show great promise in using 3DG scaffolds as conducting microenvironments for stem cell differentiation. In addition to hMSCs, cardiomyocytes and human neurons derived from induced pluripotent stem cells have also been cultured within 3DG and successfully adhere to and survive within these high graphene content constructs (FIG. 9C). These results demonstrate the potential of 3DG as a new conducting scaffold for electrogenic tissue regeneration.

Figure 6A:
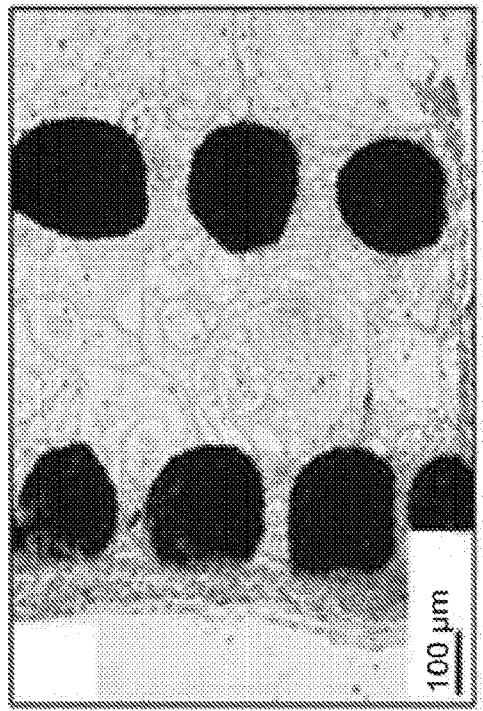
Figure 6B:
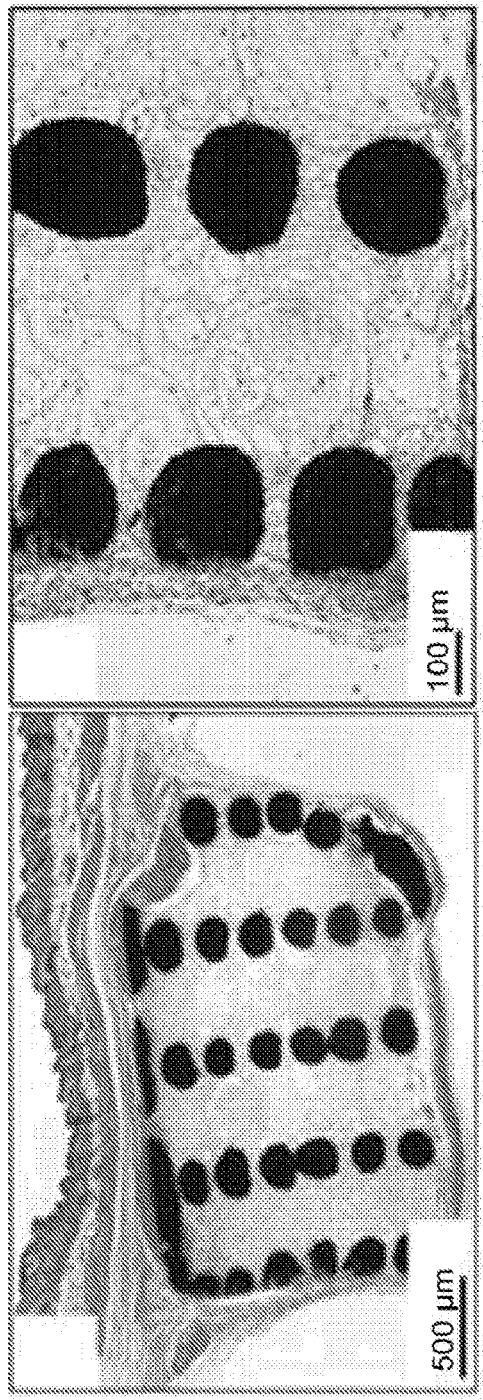
Figure 6E:
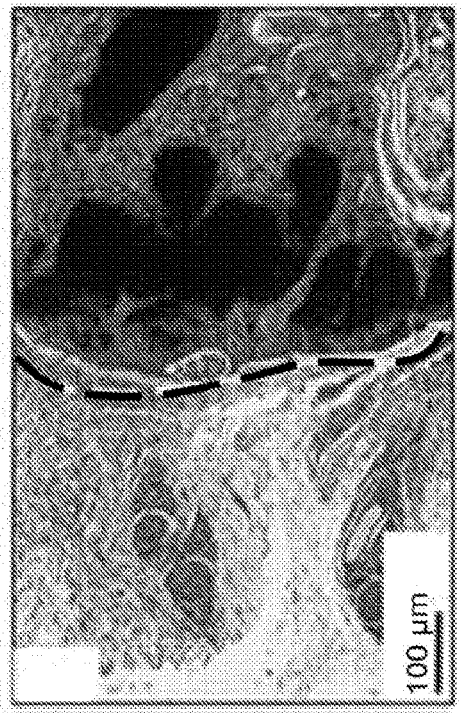
Figure 6F:
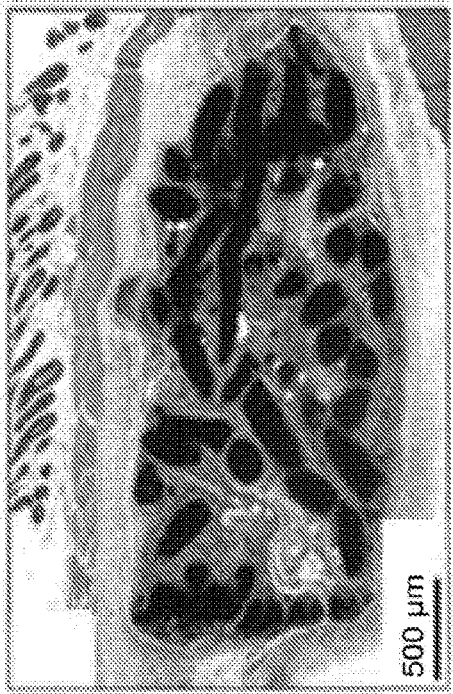
Figure 10C:
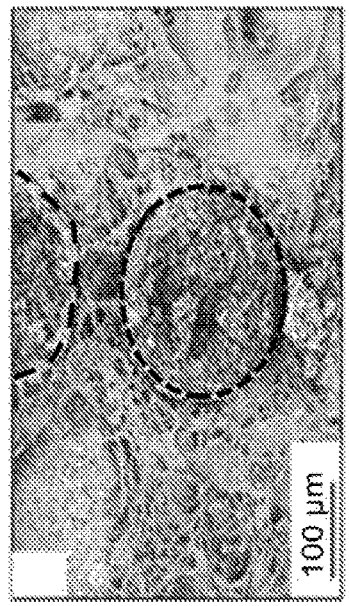
Figure 10D:
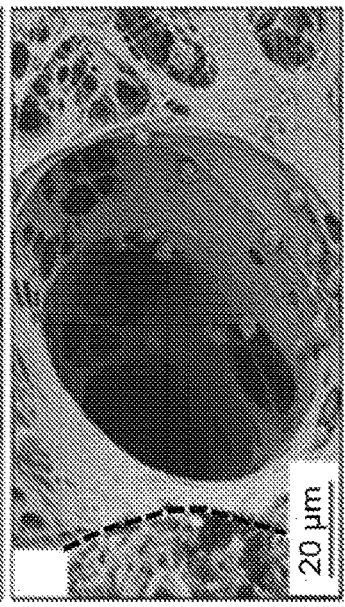
Figure 10E:
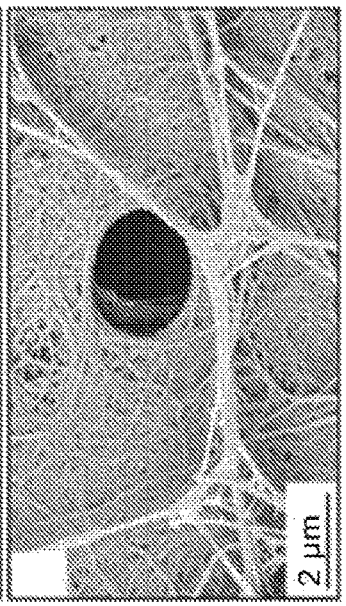
Figure 10A:
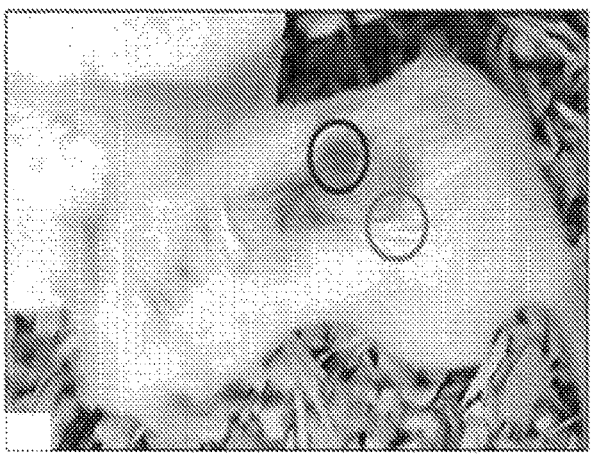
Figure 10B:
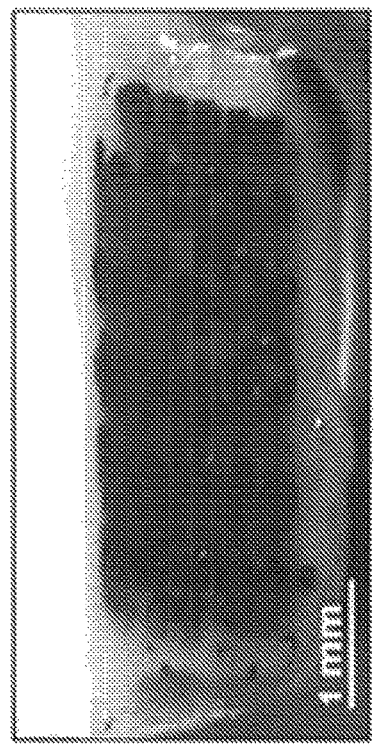
Figures 11G, 11H:
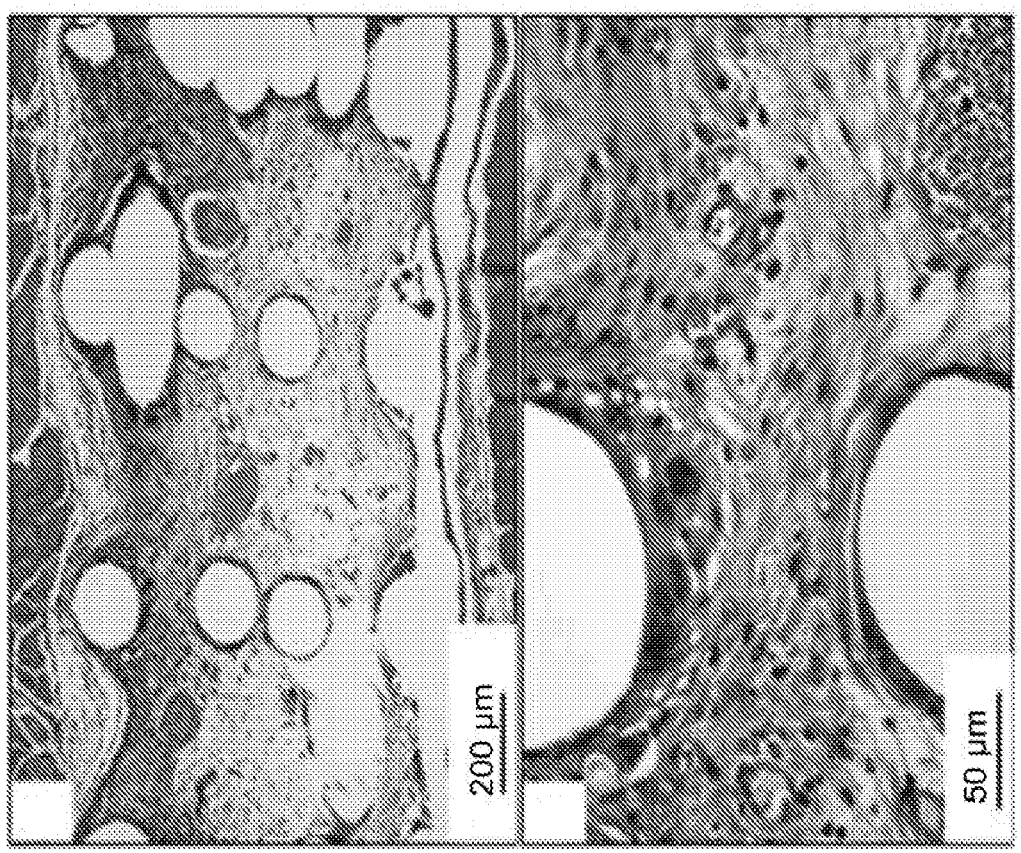

In vivo biocompatibility of 3DG was also evaluated in a mouse subcutaneous implant model. Control PLG and 3DG samples were extracted 7 and 30 days after initial implantation for histological, immunohistochemical, and SEM observations. After 7 days in vivo, there is no indication of a severe immune response or fibrous capsule formation either around individual 3DG struts or the scaffold as a whole. At this time point, a significant amount of web-like extracellular matrix (ECM) with co-centric circular morphologies, comprised primarily of collagen, was observed within the pores of the scaffold (FIG. 6A-C). SEM revealed a tissue matrix with distinct porous architectures within the 3DG (FIG. 6I, FIGS. 10C-E) that are not observed in the PLG control (FIGS. 11D-F). By day 7, cells are beginning to physically break down the 3DG around the outer edges of the scaffold (FIG. 6D). Day 7 samples stained negative for inflammatory factor COX-2 as well as macrophages (FIG. 10) further validating biocompatibility at this early time point. After 30 days in vivo, host tissue is fully integrated within the 3DG scaffolds (FIG. 6E, FIG. 10A), and significant deformation of the 3DG structure is apparent. This is expected due to the relatively soft and flexible nature of 3DG within a fully integrated, dynamic environment, such as a subcutaneous pocket. Similar to day 7, the majority of ECM within the scaffold interior is collagen (FIG. 6G). A major difference, however, is that by day 30 the ECM is considerably both more dense than day 7 and heavily vascularized, with large vessels, as well as many single cell capillaries (FIGS. 6H, J and FIGS. 10F-I). Furthermore, after 30 days, large numbers of cells are localized around the 3DG struts (FIG. 6G, FIGS. 10J, K), and there is still no evidence of fibrous capsule (i.e. dense acellular region of ECM) formation surrounding the material. These cells are confirmed to be primarily macrophages and appear to be breaking down the 3DG scaffold by physically removing individual graphene flakes and small aggregates. Gross histological analyses of the kidneys, livers, and spleens removed from mice after 30 days of 3DG and PLG scaffold implantation did not reveal the presence of any graphene flakes. This indicates that either the graphene flakes were cleared from these organs, or the graphene flakes remain in close proximity to the original implantation site after being dissociated from the main scaffold structure by macrophages. Due to the relatively large size of the graphene flakes (micron-scale), it is unlikely that they would be cleared from these organs, and more likely that they predominantly remained near the initial implant site, embedded in the surrounding tissues.

Figures 6I, 6J, 6K:
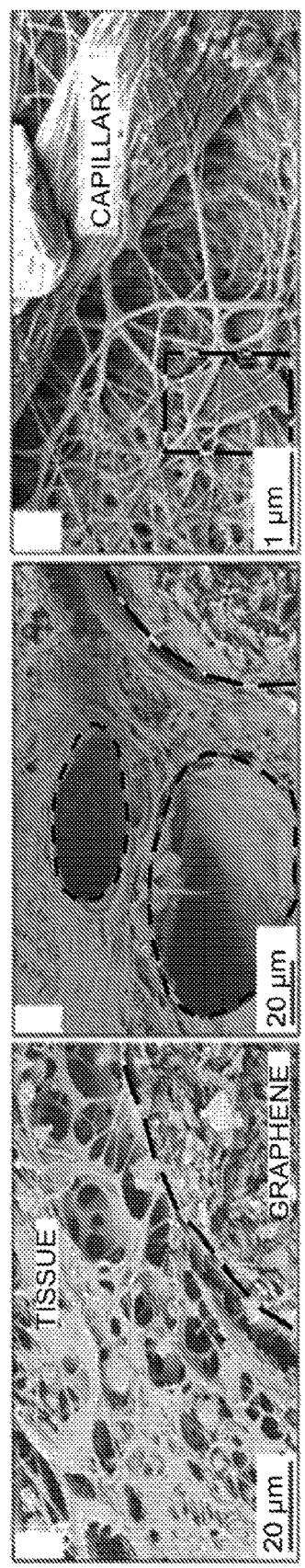

3DG biodegradability primarily depends on the hydrolysis of the PLG component of the 3DG scaffold into lactic and glycolic acids. Graphene particles are not biochemically degradable; however, it is apparent that flakes are small enough to be physically manipulated and relocated by cells (FIGS. 10I, J). Although further studies are required to determine the final, systemic destination of these graphene particles, individual particles can be observed scattered throughout and embedded within the ECM, often far from individual 3DG struts (FIG. 6K). These initial in vivo results indicate that 3DG does not elicit an inflammatory response or fibrous encapsulation at short or extended time points, and, by day 30, is actively degraded by cells—an advantageous characteristic for tissue engineering and regeneration applications where the scaffolds must break down in order to be gradually replaced by natural host tissue.

Figure 7D:
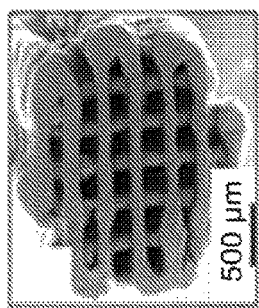
Figure 7C:
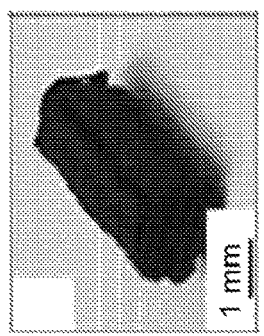
Figure 7E:
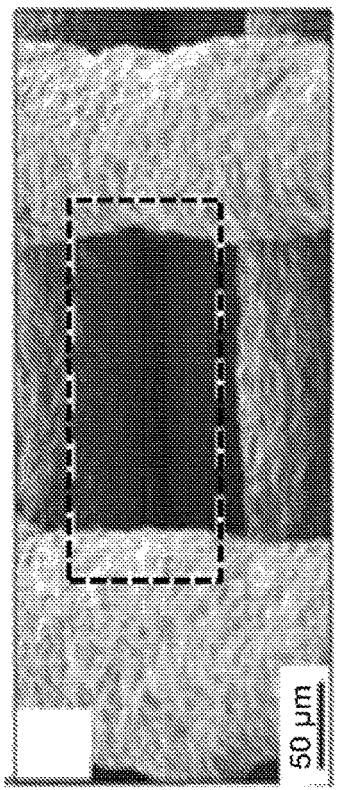
Figure 7A:
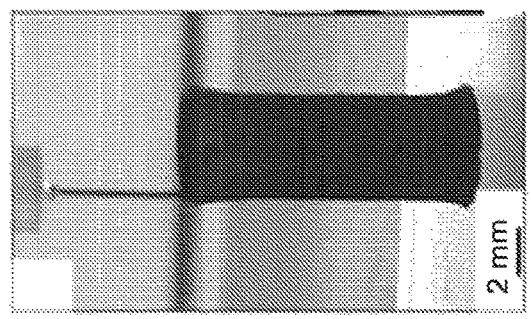
Figure 7B:
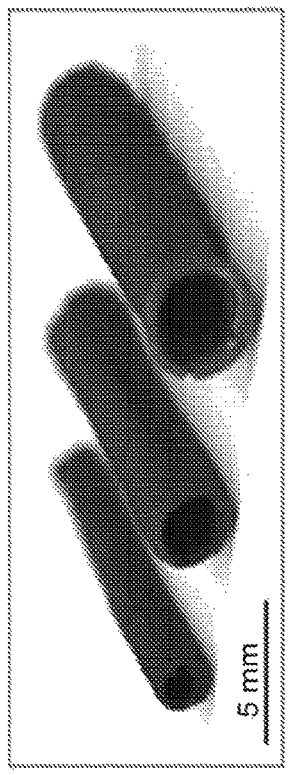

Major characteristics that are often overlooked when developing new biomaterials are surgical handling and ability to intraoperatively manipulate and form the implant to accommodate the situation. This includes being able to precisely attach the implant material, through suturing or some other means, to surrounding tissue in addition to being able to remove excess implant material from the surgical site. As a demonstration of the ability to surgically implement 3DG in clinically relevant scales, uni- (FIGS. 7A-B) and multi-channel (FIGS. 7C-E) nerve conduits, similar in architecture to those described previously were 3D printed. In addition to being able to produce relevant length 3DG nerve conduits of varying diameter (FIG. 7B), the characteristics of the ink permits rapid fabrication of high aspect ratio objects comprised of many hundreds of layers (FIG. 7F). A large stock 3DG object such as this, can be sectioned to size depending on the surgical need. In this instance, a 2 cm long section was cut from the 12 cm cylinder and sutured around and to the dorsal branch of the ulnar nerve in an unfixed human cadaver through multiple surgical steps that took advantage of the 3DG's handling physical and mechanical characteristics (FIG. 7G). After the ulnar nerve was exposed, the 2 cm section of tubular 3DG nerve conduit was longitudinally cut with surgical shears, permitting it to be wrapped around the nerve bundle. After wrapping, the longitudinal 3DG cut was sutured shut along the length of the nerve conduit. Additional sutures were used to attach the 3DG nerve conduit to the surrounding epinerium and nerve bundle (FIG. 7G, detail). Excess conduit length was then removed using surgical shears. This procedure, although performed on a cadaver, illustrates that 3DG's mechanical properties are highly advantageous for pre- and intraoperative precision surgical procedures on scales relevant to humans.

Materials and Methods

Ink Preparation.

60 (3DG), 40, and 20 vol. % graphene inks were synthesized by thorough mixing of polylactide-co-glycolide (e.g., without limitation, 85:15) copolymer (Boehringer Ingelheim, Germany), graphene powder (3-8 atomic layers thick, 5-20 µm long and wide; Graphene Laboratories Inc, USA), and a 10:2:1 by mass mixture of dichloromethane (DCM; Sigma), ethylene glycol butyl ether (Sigma), and dibutyl phthalate (Sigma), where 0.6 g dibutyl phthalate was added for every 2.2 g (1 cm$^3$) graphene. Graphene comprised 60 vol. % of the solids additions while PLG comprised the remaining 40 vol. %. Inks were allowed to thicken to a viscosity 30-35 Pa·s, as determined through use of a Brookfield DV-E rotational shear viscometer, through evaporation under ambient conditions before 3D printing. Pure PLG inks as well as 20 and 40 vol. % graphene constructs were prepared following the same protocol.

Graphene 3D-Printing.

All printed structures were fabricated using a 3D BioPlotter (EnvisionTEC GmbH, Germany). 100, 200, 400, and 1000 µm diameter polyethylene tips (Nordson EFD, USA) were used throughout the study. All 3DG inks were 3D printed onto a smooth, PTFE coated substrate. X-Y motion speeds ranged from 10 mm/s to 45 mm/s depending on the structure being fabricated. Objects could be removed from the substrate and handled immediately after printing. Applied printing pressure ranged from 0.5 bar for the 1000 µm diameter tip to 5 bar for the 100 µm tip. All ink synthesis and printing was performed at room temperature. All scaffolds for in vitro studies were created by 3D printing contoured 1.5×1.5 cm squares using a 200 µm tip; 10 layers (180 µm/layer), 200 µm spacing between deposited fibers, 0-90° fiber orientation with every other layer being offset 300 µm in X and Y relative to two layers prior. 4-mm biopsy punches were used to "punch" cylindrical scaffolds from the larger printed squares. This same procedure was used to create samples for in vivo studies, although the offset between layers was not utilized and 400 µm spacing between fibers was used. Tensile specimens were 3D printed using 200 µm diameter tips and 180 µm spacing between fibers (to ensure enough overlap to create a solid specimen). Each specimen was six printed layers thick with all layers created through fiber deposition oriented along the length of the specimen. Compression specimens were printed from 200 µm diameter tips as 2 cm-diameter, 1 cm-tall cylinders with 0.5 mm spacing between fibers and 0-90° orientation. Specimens for electrical testing were directly printed onto glass slides or PEN sheets. All electrical specimens were comprised of a single layer and a continuous fiber of known length.

Fiber Diameter and Flake Alignment Analysis.

Consistency of fiber diameter detailed in FIG. 2G was determined by first freeze fracturing a 40 layer, 0-90°, 2 cm-diameter 60 vol. % graphene scaffold printed with a 100 µm tip. The resulting cross-section was examined using SEM, and the diameter of three fibers in every third layer were measured using ImageJ. Averages and standard deviations within each layer were determined as well as the average and total standard deviation of all fibers measured. Alignment of graphene flakes was assessed by end-on cross-sectional scanning electron microscopy of graphene fibers, extruded from a 200 µm diameter tip, from within the center of a 1-cm diameter, 40 layer thick scaffold. Flake orientation in the plane of the image was measured along the major axis of the flake using ImageJ analysis software, with the angle measured with respect to the horizontal. The histogram in FIG. 2e represents the result for 122 individual flakes.

Mechanical Testing.

PLG, 3DG, and related graphene-PLG composites were 3D printed into 20 mm-gauge-length tensile specimens from respective inks Cast tensile specimens were prepared by casting 60 vol. % graphene ink into Teflon coated dishes and stamping out using a 20 mm-gauge-length tensile specimen stamp. All tensile and compression tests were performed on an LF Plus mechanical tester (Lloyd Instruments). Tensile tests were performed under constant displacement of 2 mm/min. Compressive tests were performed at a compression rate of 2 mm/min on 40 layer, 1 cm-diameter, 0-90° pattern 3DG cylinders 3D printed using a 200 µm tip. All sample groups were measured in triplicate. Elastic modulus for each was determined using a 0.2% strain offset linear slope method.

Electrical Characterization.

Unless otherwise specified, electrical measurements were carried out in air using a two-probe measurement setup with a Keithley source meter, with silver paste employed to contact the graphene fibers. Resistance measurements of single printed filaments were obtained along the direction of extrusion. Sample dimensions were measured using optical microscopy and stylus profilometry. In all cases, annealing was carried out in a tube furnace under air for 30 minutes at the specified temperature. The electrical resistance as a function of strain was monitored using a Fluke 179 digital multimeter as the printed graphene fiber was strained at a rate <0.01/s along its axis. Error bars in the measurements represent a standard deviation for 3-7 samples. Cyclic loading was performed with the PEN sheet attached to provide a well-defined and controlled strain distribution. The number of bending cycles was selected to illustrate the evolution of resistance with deformation. Because saturation in the electrical resistance is observed after ~20 cycles, going beyond 1000 cycles is unlikely to result in different behavior. All electrical properties were collected with DC measurements. It was verified that contact resistance effects were negligible using the two-probe measurement setup by varying the length of measured samples prior to more exhaustive electrical characterization.

To analyze the scaling behavior of the resistance of 3D printed graphene objects, consider the relationship between the measured resistance and the cross-sectional area of printed fibers. In general, the resistance relates to the cross-sectional area by a power law relationship of the form $$R = c * A^x$$

where R is the resistance, c is a proportionality constant reflecting intrinsic material properties as well as geometry, A is the cross-sectional area, and x is the power law exponent, which reflects the conduction path. For linear conduction through a uniform, bulk material, this exponent is −1 because the entire cross-sectional area is active. If the conduction path is restricted to the surface of the material, this exponent is −½, as only the perimeter of the cross section is electrically active. The slope of a linear fit to a plot of log(R) vs. log(A) gives the value of the power law exponent, x.

This analysis was performed for the 3D printed graphene fibers extruded from tips of varying diameters, as shown in FIG. 8B. The fitted value of $x = -0.79 \pm 0.03$ suggests that, while bulk conduction is present, enhanced conduction along the fiber surface is also evident. This analysis has limitations, as the detailed microstructure of different samples is dependent on the extrusion flow field, which varies for different diameter filaments.

In Vitro Cell Seeding.

Passage 2 human bone marrow derived mesenchymal stem cells (hMSCs; Lonza, Walkersville) were expanded up to passage 5 using MSC basal medium and proliferation kit (Lonza, Walkersville) according to the vendor's instructions. iCell® Neurons (Cellular Dynamics International, USA) were thawed and suspended in vendor-provided iCell® Neuron medium. Prior to cell seeding, 3DG and PLG scaffolds were rinsed in 70% ethanol for 1 hour followed by three 4 minute rinses in sterile phosphate buffered saline (PBS). As shown through previous work, this not only sterilizes the scaffolds, but also removes residual solvents. Scaffolds were stored in PBS until cell seeding. 50,000 hMSCs were seeded into each scaffold via injection of 7 µL cell-suspensions in a medium comprised of: 1× low glucose Delbeco's Modified Eagle Medium (DMEM) modified with 10% fetal bone serum, HEPES (4-(2-hydroxyethyl)-1-piperazineethanesulfonic acid) buffer, L-glutamine, and 10 units antibiotic antimyotic (Invitrogen). 200,000 iCell® Neurons suspended in iCell® Neuron medium (Cellular Dynamics International) were added to each scaffold in 10 µL aliquots. 500 µL of respective media was added to each well 1 hour after initial seeding. All cell-seeded samples were incubated at 37° C. in 5% $CO_2$. Materials and methods related to in vitro characterization, including imaging, DNA quantification, and gene expression via real-time polymerase chain reaction (PCR) analysis may be found in Examples 7a-e, below.

Additional 3DG 3D Printing.

Single and multi-channel nerve guides shown in FIG. 7 were 3D printed from 3DG inks using a 250 µm tip and 140 µm layer spacing. The 3DG skull in FIG. 7I was 3D printed from 3DG using a reduced-scale .STL file initially found on an open-source database.

Live/Dead Analysis.

Samples reserved for confocal fluorescence imaging at day 1, 7, and 14 timepoints were first rinsed in sterile PBS and incubated in a PBS solution of 5 mM calcein AM and 5 mM ethidium bromide homodimer (Invitrogen) for 30 minutes prior to imaging. A Nikon C2+ fluorescent scanning confocal microscope was used to obtain a series of images through the top ~500 µm of each sample. Images were reconstructed into projections of 3D representations using ImageJ (NIH).

Cell Number Quantification.

Specified samples at each of 1, 7, and 14 day time points were prepared for DNA quantification measurements by first lysing cells via sonication for 45 minutes at room temperature in 1 mL of 0.02 wt. % triton-X 100 (Bio-Rad) solution in DNA-free water, Lysates were stored at −80° C. until the quantification was performed at the end of the 2 week period. Double stranded DNA within cell lysates was quantified via fluorescent assay using Quanti-iT™ Picogreen® dsDNA Assay Kit (Invitrogen) according to the manufacturer's instructions. Number of cells as a function of material and time point was obtained through first determining dsDNA/cell by using P5 hMSC lysates derived from known cell-number aliquots. The resulting dsDNA/cell value (0.66±0.02 pg/cell) was used to convert total mass dsDNA content per scaffold into total number of cells.

Real-Time PCR and Gene Expression Analysis.

At 7 and 14 days after seeding, RNA was extracted from individual scaffold samples (n=3) with TRIzol (Lifetech) and reverse transcribed into cDNA using iScript Reverse Transcription Supermix® (Bio-Rad). cDNA was stored at −80° C. until gene expression analysis was performed. An iQ™ SYBR® Green Super Mix (Bio-Rad) was used in conjunction with forward and reverse primers (sequences not shown) for glyceraldehyde-3-phosphate dehydrogenase (GAPDH; housekeeping gene), nestin (Nes), neuron-specific class III β-Tubulin (TuJ1), microtubule-associated protein 2 (MAP2), and glial fibrillary acidic protein (GFAP). These primer sequences were provided and had been previously designed by Seth Lee (Laboratory of Samuel Stupp, Northwestern University). Three samples from each group were analyzed. Real-time quantitative PCR was performed on an IQ5PCR (Bio-Rad). PCR conditions were as recommended by Advanced Tissue Resources Core, Harvard NeuroDiscovery Center: cDNA denaturation at 95° C. for 6 min, followed by 50 repeated cycles at 95° C. for 30 s, annealing at 55° C. for 30 s, and extension at 72° C. for 45 s. Threshold values for each gene were translated to ddct$^2$ values through normalization to the corresponding sample GAPDH threshold values. Resulting ddct$^2$ values were further normalized to ddct$^2$ values obtained from unseeded (Day 0) passage 5 hMSCs (from same flask of cells used to seed samples) to obtain fold change values over the initial undifferentiated state.

Scanning Electron Microscopy.

Samples without cells were prepared for SEM (LEO Gemini 1525) by coating with 15 nm osmium metal via osmium plasma (Osmium Coater, SPI Supplies) prior to imaging. Samples from in vitro studies were prepared directly from samples imaged with Live/Dead® staining. Immediately after confocal fluorescence imaging, samples were submerged in a fixative solution of 3 wt. % sucrose (Sigma) and 2 wt. % glutaraldehyde (Sigma) solution for 30 minutes. Samples were further dehydrated through graded (80, 90, 100%) ethanol treatments for 10 minutes each followed by critical point drying (Critical Point Dryer, Tousimis Samdri), and coated with 15 nm osmium prior to imaging (LEO Gemini 1525). In vivo samples were prepared by fixing in fixative solution for 45 minutes. Half of each sample was stored in 70% ethanol in preparation for SEM, while the other half was stored in 10% formaline and reserved for histology. In preparation for SEM, in vivo samples were removed from 70% ethanol and processed similarly to the previously discussed in vitro samples.

Subcutaneous Scaffold Implantation and In Vivo Sample Characterization.

A single subcutaneous incision was made on the back of each female BALB/c mouse near the nape of the neck. A PLG scaffold was inserted under the skin and pushed to the left side of the mouse. A 3DG scaffold was inserted through the same incision and pushed to the right side of the back. Incisions were sutured closed using a single suture. Daily care for mice was administered by staff from Northwestern University's Center for Comparative Medicine. Mice were monitored daily by authors. Mice were sacrificed at 7 and 30 days (n=2), at which point scaffolds and surrounding tissue were removed and prepared for further analysis. The surgical protocol followed NIH guidelines for the care and use of laboratory animals and was approved by Northwestern University's Animal Care and Use Committee (Chicago, Ill., USA).

Histology.

Explanted in vivo samples were fixed in 10% formalin for two weeks prior to paraffin embedding, processing, and staining (H&E, Masson's Trichrome, COX-2, CD45) was performed by Northwestern University's Mouse Histology and Phenotyping Laboratory using established standard histological and immunohistological protocols. Gross kidney, liver, and spleen H&E processing was performed on organs collected from mice immediately upon sacrifice and collection of explanted scaffolds. Organs were fixed in 10% formalin for up to 1 week prior to paraffin embedding, processing and staining using standard histological protocols. All histology slides were imaged using an upright optical microscope (Nikon).

Nerve Conduit Implantation in Human Cadaver.

A 2 cm long section was preemptively cut from the as-printed 12 cm long 3DG nerve conduit cylinder (FIG. 7F) using a scalpel. The dorsal branch of the ulnar nerve in an unfixed human cadaver was exposed and the 3DG nerve conduit was cut longitudinally and wrapped around the intact nerve. The 3DG nerve conduit was stitched to the epineurium using a 7-0 prolene suture. Excess 3DG conduit length was then intraoperatively trimmed. Finally, the nerve was transected and two additional sutures were used to attached the nerve to the 3DG nerve conduit.

Statistical Analyses.

Tensile specimens were tested with n=4. Sample sizes for electrical tests ranged between 3 and 7. Two tail t-tests were utilized to determine significance between groups with a confidence level of 0.05.

As demonstrated, using a solution-based, scalable ink, graphene can be 3D printed under ambient conditions into arbitrarily shaped scaffolds with filaments ranging in diameter from 100 to 1000 μm. Although we primarily focus on simple architectures in this work for the purposes of material and biological characterization and evaluation, much more complex structures can be 3D printed with ease (FIGS. 7H-I), elevating this 3DG ink above many other direct ink write systems that are only capable of producing simple structures comprised of a maximum of several layers. This particular composite system, with a tunable graphene composition, has unique mechanical, electrical, biological, and surgical handling properties. Not only does 3DG display the highest electrical conductivity of any carbon-based 3D printed material reported to date, it is also mechanically flexible, biocompatible, neurogenically bioactive, biodegradable, and surgically friendly. These characteristics enable a range of potential applications in wearable and implantable electronics, sensors, and tissue engineering. In vitro studies confirmed that 3DG supports the viability of multiple, distinct cell types, including adult mesenchymal stem cells, which develop neuron-like morphological characteristics, as well as a large upregulation of glial and neuron-specific genes in the absence of exogenous neurogenic factors. This suggests that 3DG could have possible practical applications in nerve tissue engineering and regeneration as single and multi-channel nerve guides (FIG. 7). In vivo studies with 3D printed graphene also suggest that it is biocompatible, with no evidence of graphene flakes collecting in the kidney, liver, or spleen. If the previous characteristics existed without the ability to be surgically handled and implemented, 3DG would primarily be relegated to being a research tool. However, we have also demonstrated that it can be cut, sutured, and manipulated intraoperatively for fine surgical procedures, such as nerve bundle wrapping. By concurrently achieving advances in electrical, mechanical, biological, and handling properties, combined with its ease of processing and fabrication into complex, user-defined structures, 3DG is poised to accelerate the development and manufacturing of emerging functional electronic and medical devices.

What is claimed is:

1. An implantable tissue growth structure, wherein the structure is a three-dimensional, biocompatible, biodegradable, electrically conductive structure comprising a network of fibers, the fibers comprising a composite comprising graphene flakes in a polymeric matrix, wherein the composite has a graphene flake content of at least 40 vol. %.

2. The structure of claim 1, wherein the fibers are arranged in an ordered, three-dimensional grid.

3. The structure of claim 1, wherein the graphene flakes along the surfaces of the fibers are preferentially aligned along the long axes of the fibers.

4. The structure of claim 3, wherein the fibers have higher electrical conductivities at their surfaces than in their bulk.

5. The structure of claim 1, wherein the structure is seeded with stem cells.

6. The scaffold of claim 1, wherein the polymeric matrix comprises polylactic acid, glycolic acid, copolymers of polylactic acid and glycolic acid, polycaprolactone, or a mixture thereof.

7. The structure of claim 1, wherein the network of fibers comprises fibers having diameters of 93.5 μm or greater.

8. The structure of claim 7, wherein the network of fibers comprises fibers having diameters in the range from 100 μm to 1000 μm.

9. The structure of claim 1, wherein at least some of the fibers are fused with adjacent, non-parallel fibers.

10. A method for generating electrogenic cells or tissues, the method comprising:
contacting a three-dimensional, biocompatible, biodegradable, electrically conductive structure with electrogenic cells or electrogenic tissue, wherein the structure comprises a network of fibers, the fibers comprising a composite of graphene flakes in a polymeric matrix, and further wherein the composite has a graphene flake content of at least 40 vol. %, wherein electrogenic cell generation takes place on the scaffold.

11. The method of claim 10 further comprising contacting the structure with stem cells, wherein the electrogenic cell generation takes place by allowing the stem cells to differentiate into electrogenic cells.

12. The method of claim 11, wherein the stem cells are human mesenchymal stem cells.

13. The method of claim 11, wherein contacting the structure with stem cells comprises seeding the structure with stem cells, and further wherein allowing the stem cells to differentiate into electrogenic cells comprises culturing the cell-seeded structure in a culture medium.

14. The method of claim 13, wherein the culture medium is free of neuronal differentiating biochemical factors.

15. The method of claim 11, wherein contacting the structure with electrogenic cells or electrogenic tissue comprises implanting the structure into electrogenic tissue in a living subject.

16. The method of claim 15, further comprising seeding the structure with stem cells prior to implanting it into the electrogenic tissue in the living subject, wherein signals from the electrogenic tissue induce the differentiation of the stem cells into electrogenic cells.

17. The method of claim 16, wherein the electrogenic cells are neurogenic cells.

18. The method of claim 17, wherein the structure is characterized in that it is able to induce neurogenic differentiation without the need for neuronal differentiating biochemical factors.

19. The method of claim 17, wherein the composite has a graphene flake content of at least 60 vol. %.

20. The method of claim 17, wherein the stem cells are human mesenchymal stem cells.

21. The method of claim 15, wherein the structure is implanted such that it connects a nerve end or nerve bundle to another nerve end or nerve bundle, or to electrogenic tissue in the living subject, wherein the structure acts as a nerve guide by directing nerve generation along its length.

22. The method of claim 15, wherein the scaffold is implanted such that it connects a first segment of muscle tissue to a second segment of muscle tissue in the living subject, wherein the scaffold acts as a tissue growth guide by directing muscle tissue generation along its length.

23. The method of claim 22, wherein the muscle tissue is cardiac tissue.

* * * * *